United States Patent [19]

Töpfl et al.

[11] Patent Number: 4,940,792
[45] Date of Patent: Jul. 10, 1990

[54] HERBICIDAL SULFONYLUREAS

[75] Inventors: Werner Töpfl, Dornach; Willy Meyer, Riehen, both of Switzerland; Hans-Dieter Schneider, Weil am Rhein, Fed. Rep. of Germany

[73] Assignee: Ciba-Geigy Corporation, Ardsley, N.Y.

[21] Appl. No.: 128,761

[22] Filed: Dec. 4, 1987

Related U.S. Application Data

[62] Division of Ser. No. 53,912, May 26, 1987, Pat. No. 4,764,203, which is a division of Ser. No. 699,388, Feb. 7, 1985, Pat. No. 4,685,961.

Foreign Application Priority Data

Feb. 14, 1984 [CH] Switzerland ............................ 720/84
Apr. 12, 1984 [CH] Switzerland ............................ 1841/84

[51] Int. Cl.$^5$ ................. C07D 239/42; C07D 401/12; C07D 403/12; C07D 413/12
[52] U.S. Cl. .................................... 544/321; 544/122; 544/123; 544/320; 544/323; 544/324; 544/330; 544/331; 544/332; 540/601
[58] Field of Search ............... 544/320, 321, 323, 324, 544/330, 331, 332, 122, 123; 540/601

[56] References Cited

U.S. PATENT DOCUMENTS 4,689,070 8/1987 Shapiro ............................... 544/320

Primary Examiner—John M. Ford
Attorney, Agent, or Firm—Kevin T. Mansfield; Edward McC. Roberts

[57] ABSTRACT

Novel substituted N-sulfonyl-N'-pyrimidinylureas or N-sulfonyl-N'-triazinylureas of the formula I

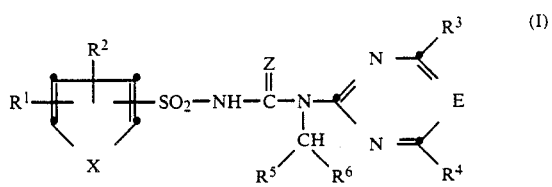

have good pre- and postemergence selective herbicidal and growth regulating properties.

In this formula
E is nitrogen or —CH=,
the group

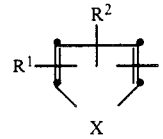

is a phenyl, naphthyl, furyl, thiophenyl, pyrrole or pyridinyl radical which is substituted in accordance with the definitions of
$R^1$ and $R^2$,
$R^3$ and $R^4$ are hydrogen, lower alkyl or lower alkoxy, or one of $R^3$ and $R^4$ may also be halogen, lower alkenyl, lower haloalkenyl, lower haloalkoxy, amino, lower alkylamino, —CH(OCH$_3$)$_2$, a cyclized ketal group or a saturated 5- or 7-membered heterocycle which is bound through the nitrogen atom,
$R^5$ is hydrogen, lower alkyl, lower haloalkyl, or an unsubstituted or substituted phenyl, benzyl or naphthyl radical, and
$R^6$ is an alkyl, acyl or acylamido radical which is bound through sulfur or a sulfinyl or sulfonyl group and is as defined in the description, or is a 5- to 7-membered heterocyclic amino radical which is bound through the nitrogen atom.

These compounds are particularly suitable for selectively controlling weeds in crops of cereals.

10 Claims, No Drawings

HERBICIDAL SULFONYLUREAS

This is a division of application Ser. No. 053,912, filed 5/26/87, now U.S. Pat. No. 4,764,203, which is a division of application Ser. No. 699,388, filed 2/7/85, now U.S. Pat. No. 4,685,961.

The present invention relates to novel substituted N-sulfonyl-N'-pyrimidinylureas and N-sulfonyl-N'-triazinylureas and salts thereof with herbicidal and plant growth regulating properties, to the preparation thereof, to compositions containing them and to the use thereof for controlling weeds, in particular selectively, in crops of useful plants, or for regulating and inhibiting plant growth. The invention further relates to novel pyrimidin-2-ylureas and triazin-ylalkylamines prepared as intermediates.

The substituted N-sulfonyl-N'pyrimidinylureas and N-sulfonyl-N'-triazinylureas of this invention have the formula I

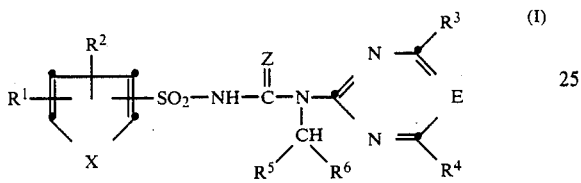

wherein
E is nitrogen or —CH=,
X is oxygen, sulfur, —NR$^7$, —N=CR$^7$, —CH=CH— or

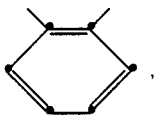

Y is oxygen or an $S(O)_m$ radical,
m is 0 or an integer from 1 to 2,
Z is oxygen or sulfur,
R$^1$ is hydrogen, halogen, nitro, C$_1$–C$_4$alkyl, C$_1$–C$_4$haloalkyl, C$_2$–C$_4$alkenyl, C$_2$–C$_4$haloalkenyl, C$_2$–C$_4$alkynyl, an amino group NR$^{10}$R$^{11}$, a ketal radical —CR$^7$(OC$_1$–C$_7$alkyl)$_2$ or

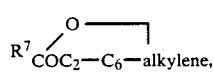

a tetrahydrofuran-2-yloxy or tetrahydropyran-2-yloxy radical, —OSO$_2$R$^8$, —COR$^8$,

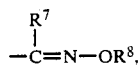

—SO$_2$NR$^{10}$R$^{11}$, SO$_2$R$^8$, YR$^8$, phenyl, benzyl or phenoxy, wherein the phenyl nucleus can be substituted by one or more identical or different members selected from the group consisting of halogen, nitro, C$_1$–C$_4$alkyl, C$_1$–C$_4$haloalkyl or C$_1$–C$_4$alkoxy,
R$^2$ is hydrogen, halogen, C$_1$–C$_4$alkyl, C$_1$–C$_4$alkoxy, C$_1$–C$_4$haloalkyl or nitro,
R$^3$ and R$^4$, each independently of the other, are hydrogen, halogen, C$_1$–C$_4$alkyl, C$_1$–C$_4$alkoxy, C$_1$–C$_4$haloalkyl, C$_1$–C$_4$haloalkoxy, C$_1$–C$_4$alkylthio, C$_2$–C$_4$alkoxyalkyl, C$_2$–C$_4$alkoxyalkoxy, cyclopropyl, NH$_2$, C$_1$–C$_4$alkylamino, di(C$_1$–C$_4$)alkylamino or a 5- to 7-membered nitrogen-containing heterocycle which is bound through the nitrogen atom and which may contain a further hetero atom, or are a —CH(OCH$_3$)$_2$ or

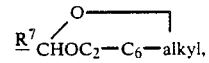

radical,
R$^5$ is hydrogen, C$_1$–C$_4$alkyl, C$_1$–C$_4$haloalkyl, or a phenyl, benzyl, furyl, thienyl or naphthyl radical, each of which is unsubstituted or substituted by one or more identical or different members selected from the group consisting of halogen, nitro, C$_1$–C$_4$alkyl, C$_1$–C$_4$haloalkyl or C$_1$–C$_4$alkoxy,
R$^6$ is an —S(O)$_m$R$^9$ radical or a 5- to 7-membered heterocyclic radical which is bound through a nitrogen atom and may contain further hetero atoms in the ring and may be fused to a benzene ring and is unsubstituted or substituted by one or more identical or different members selected from the group consisting of nitro, halogen or C$_1$–C$_4$alkyl,
R$^7$ is hydrogen, C$_1$–C$_4$alkyl, C$_1$–C$_4$haloalkyl, C$_5$–C$_6$cycloalkyl, C$_4$–C$_7$cycloalkyl, C$_2$–C$_4$alkoxyalkyl, C$_2$–C$_4$alkenyl, C$_2$–C$_4$haloalkenyl, C$_5$–C$_6$cycloalkenyl, C$_3$–C$_4$alkynyl, C$_1$–C$_4$cyanoalkyl, C$_1$–C$_4$alkyl-NR$^9$R$^{10}$, benzyl or benzyl which is substituted by halogen,
R$^8$ is C$_1$–C$_4$alkoxy or has the same meaning as R$^7$ but is not hydrogen,
R$^9$ is a C$_1$–C$_4$alkyl radical which can be substituted by halogen, C$_2$–C$_4$alkoxy, carboxyl, C$_1$–C$_4$alkoxycarbonyl or —CONR$^{10}$R$^{11}$, or is a phenyl, benzyl or naphthyl radical, each of which can be substtiuted by one or more identical or different members selected from the group consisting of halogen, nitro, carboxyl, C$_1$–C$_4$alkyl, C$_1$–C$_4$haloalkyl, C$_1$–C$_4$alkoxy or C$_1$–C$_4$haloalkoxy, and in an —SR$^9$ radical R$^9$ can also be a radical selected from —CZ—C$_1$–C$_4$alkyl, —CZO—C$_1$–C$_4$alkyl, —CZNR$^{10}$R$^{11}$, —CZ-phenyl, CZ-benzyl or CZ-naphthyl, wherein the phenyl rings may be substituted as indicated above,
R$^{10}$ and R$^{11}$, each independently of the other, are hydrogen, C$_1$–C$_4$alkyl, C$_3$–C$_4$alkenyl, C$_3$–C$_4$alkynyl, C$_1$–C$_4$cyanoalkyl, or one of R$^{10}$ and R$^{11}$ may also be C$_1$–C$_4$alkoxy or C$_2$–C$_4$alkoxyalkyl, phenyl or benzyl, and the phenyl ring may be substituted by one or identical or different members selected from the group consisting of halogen, nitro, C$_1$–C$_4$alkyl, C$_1$–C$_4$haloalkyl or C$_1$–C$_4$alkoxy; or R$^{10}$ and R$^{11}$, together with the nitrogen atom to which they are attached, may also be a 5- to 7-membered saturated or partially saturated heterocycle which may contain a further nitrogen or sulfur atom in the ring and/or one or two further nitrogen atoms, and which may be substituted by halogen and/or C$_1$–C$_4$alkyl.

The invention also relates to the salts of these sulfonylureas with organic and inorganic bases.

Herbicidal ureas, triazines and pyrimidines are generally known in the art. Sulfonylureas with herbicidal and plant growth regulating properties have recently been described for example in European patent applications 44211, 44807 and 44808, and also in UK patent applications 2 112 783 and 2 112 784.

Alkyl in the above definitions denotes straight chain or branched alkyl, for example methyl, ethyl, n-propyl, isopropyl or the 4 isomers of butyl.

Alkoxy is methoxy, ethoxy, n-propoxy, isopropoxy, the 4 isomers of butoxy, n-amyloxy, isoamyloxy, 2-amyloxy or 3-amyloxy, with methoxy, ethoxy or isopropoxy being preferred.

Halogen by itself or as moiety of haloalkoxy, haloalkyl or haloalkylthio denotes fluorine, chlorine and bromine, with fluorine and chlorine being preferred.

Within the scope of this invention, the radicals defined for $R^6$ comprise for example the following radicals:

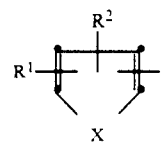

radical is a phenyl radical which is substituted in the ortho-position by $R^1$, $R^6$ is an $-S(O)_m R^8$ radical, $R^6$ is a 5- to 7-membered heterocycle which is bound through the nitrogen atom and may contain further hetero atoms in the ring, and may be fused to a benzene ring and may be unsubstituted or substituted by one or more members selected from the group consisting of nitro, halogen and/or $C_1$–$C_4$alkyl.

Preferred compounds are for example those of the

| | | |
|---|---|---|
| $-S-C_1-C_4$alkyl | $-S-CH_2COOC_1-C_4$alkyl | phenylthio-$SCH_2COOH$ |
| $-SO-C_1-C_4$alkyl | $-S-CH_2CONHC_1-C_4$alkyl | benzylthio-$SCH(CH_3)COOH$ |
| $-SO_2C_1-C_4$alkyl | $-S-CH_2CON(C_1-C_4$alkyl$)_2$ | benzoylthio |
| $-S-CO-C_1-C_4$alkyl | $-S-CS-OC_1-C_4$alkyl | $-SCSN(C_1-C_4$alkyl$)_2$ | formula Ic as well as the following heterocyclic amino radicals: 1,2,4-triazolyl, 1,2,3,4-tetrazol-1-yl, pyrazol-1-yl, imidazol-1-yl, benztriazol-1-yl, benzimidazol-1-yl, indol-1-yl, indadzol-1-yl, pyrimidin-1-yl, pyridazin-1-yl, pyrazin-1-yl, which rings may be substituted by one to three members selected from nitro, halogen, preferably chlorine or bromine, and/or $C_1$–$C_4$alkyl, preferably methyl.

The 5- to 7-membered saturated or partially saturated heterocyclic radicals falling within the definition of the amino radical $NR^{10}R^{11}$ comprise for example the following radicals: pyrrolidino, piperidino, morpholino, thiomorpholino, azepino, imidazol-1-yl, triazol-1-yl, 1,3-oxazol-3-yl, 1,3-thiazol-1-yl, piperazin-1-yl, which radicals may be unsubstituted or sdubstituted by halogen, preferably chlorine or bromine and/or by $C_1$–$C_4$alkyl, preferably methyl.

Alkoxyalkyl radicals are methoxymethyl, ethoxymethyl, methoxyethyl and ethoxyethyl, with methoxyethyl being preferred. Within the scope of this invention, alkoxyalkyl radicals are methoxymethoxy, ethoxymethoxy, methoxyethoxy and ethoxyethoxy. Haloalkyl by itself or as moiety of another substituent such as haloalkoxy or haloalkylthio is usually chloromethyl, fluoromethyl, difluoromethyl, trifluoromethyl, 2-chloroethyl, 2,2,2-trifluoroethyl, 1,1,2,2-tetrafluoroethyl, pentafluoroethyl, 1,1,2-trifluoro-2-chloroethyl, 2,2,2-trifluoro-1,1-dichloroethyl, pentachloroethyl, 3,3,3-trifluoropropyl, 2,3-dichloropropyl, and 1,1,2,3,3,3-hexafluoropropyl. Fluoromethyl, chloromethyl, difluoromethyl and trifluoromethyl are preferred.

Preferred compounds of formula I are those wherein either
Z is an oxygen atom,
the

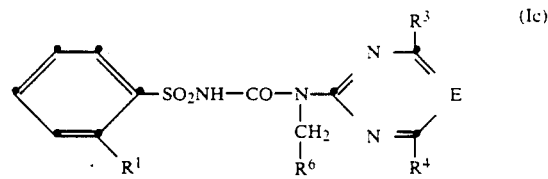

wherein E, $R^1$, $R^3$, $R^4$ and $R^6$ are as defined for formula I; and those of the general formula Id

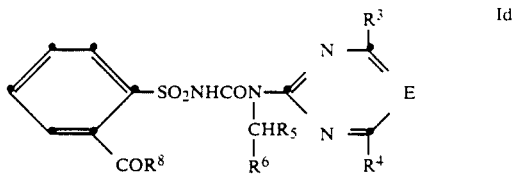

wherein E, $R^3$, $R^4$, $R^5$, $R^6$ and $R^8$ are as defined for formula I.

The compounds of formula I are prepared for example by the following methods.

A first process comprises reacting a sulfonyl isocyanate of formula II

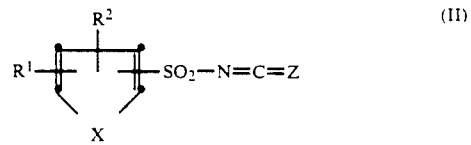

wherein $R^1$, $R^2$, X and Z are as defined for formula I, with the equivalent amount of a 2-aminopyrimidine or 2-aminotriazine of formula III

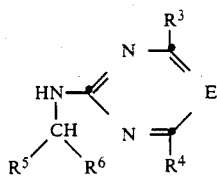

wherein E, $R^3$, $R^4$, $R^5$ and $R^6$ are as defined for formula I, in an inert organic solvent or diluent, and, if desired, isolating the resultant urea in the form of a salt or converting it into a salt with an inorganic or organic base.

A second process for obtaining the compounds of formula I comprises reacting a sulfonylamide of formula IV

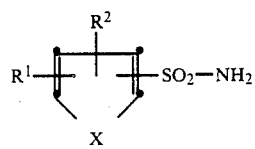

wherein $R^1$, $R^2$ and X are as defined for formula I, with the equivalent amount of a 2-pyrimidinyl- or 2-triazinyl-carbamoylhalide of formula V

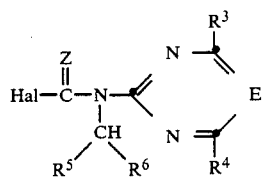

wherein Hal is a halogen atom, preferably chlorine or bromine, and E, $R^3$, $R^4$, $R^5$, $R^6$ and Z are as defined for formula I, in an inert solvent or diluent and in the presence of a base, and, if desired, isolating the resultant urea in the form of a salt or converting it into a salt with an inorganic or organic base.

A third process for obtaining the compounds of formula I comprises reacting a sulfonylurea of formula VI

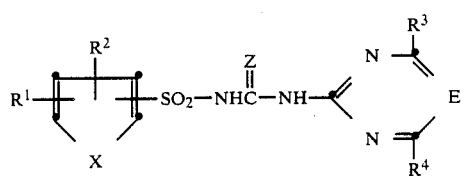

wherein E, $R^1$, $R^2$, $R^3$, $R^4$, X and Z are as defined for formula I, with the equivalent amount of a methyl halide of formula VII

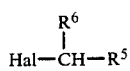

wherein Hal is a halogen atom, preferably a chlorine or bromine atom, and $R^5$ and $R^6$ are as defined for formula I, in an inert solvent or diluent and in the presence of a base, and, if desired, isolating the resultant urea in the form of a salt or converting it into a salt with an inorganic or organic base.

If desired, the ureas of formula I can be converted into basic addition salts with amines, alkali metal hydroxides or alkaline earth metal hydroxides or with quaternary ammonium bases. This is done for example by reacting the urea with the equimolar amount of base and removing the solvent by evaporation. Such reactions are known and are described for example in U.S. Pat. Nos. 2 834 757 and 3 410 887.

It is convenient to carry out these reactions for obtaining compounds of formula I in aprotic, inert organic solvents.

Examples of such solvents are hydrocarbons such as benzene, toluene, xylene or cyclohexane; chlorinated hydrocarbons such as methylene chloride, chloroform, carbon tetrachloride, or chlorobenzene; ethers such as diethyl ether, ethylene glycol dimethyl ether, diethylene glycol dimethyl ether, tetrahydrofuran or dioxan; nitriles such as acetonitrile or propionitrile; amides such as dimethylformamide, diethylformamide or N-methylpyrrolidinone.

The reaction temperatures are preferably in the range from $-20°$ to $+120°$ C. The coupling reactions are normally slightly exothermic and can be carried out at room temperature. To shorten the reaction time or also to initiate the reaction it is expedient to heat the reaction mixture briefly to boiling point. The reaction times can also be shortened by addition of a few drops of a base or isocyanate as catalyst. Preferred bases are tertiary amines such as trimethylamine, triethylamine, quinuclidine, 1,4-diazabicyclo[2,2,2]octane, 1,5-diazabicyclo[4,3,0]-non-5-ene or 1,8-diazabicyclo[5,4,0]undec-7-ene. However, the bases employed may also be inorganic bases, e.g. hydrides such as sodium hydride or calcium hydride, hydroxides such as sodium hydroxide or potassium hydroxide, carbonates such as sodium or potassium carbonate, or bicarbonates, such as potassium or sodium bicarbonate.

The final products of formula I can be isolated by concentrating the reaction mixture and/or removing the solvent by evaporation, and by recrystallisation or by triturating the solid residue in a solvent in which it is poorly soluble, such as an ether, an aromatic hydrocarbon or a chlorinated hydrocarbon.

In addition to these general methods of preparing the compounds of formula I, and depending on the meanings of the substituents $R^5$ and $R^6$, further synthesis paths, each of which is suitable only for one specific group of final products, are also possible. Such syntheses are illustrated in the following schemes. In the formulae below, E, m, $R^1$, $R^2$, $R^3$, $R^4$, $R^5$, $R^6$, $R^8$, X and Z are as defined for formula I. The Roman numerals I, II and IV denote the formulae so numbered above.

Scheme 1

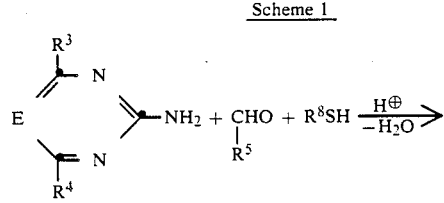

VIII

-continued
Scheme 1

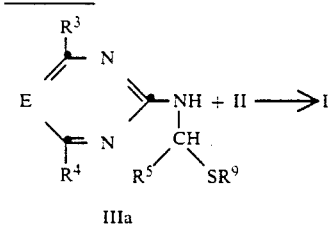

IIIa

A 2-aminopyridine or a 2-amino-1,3,5-triazine of formula VIII is condensed with an aldehyde to give the Schiff's base, which is reacted in situ with the mercapto compound. The reaction is carried out at elevated temperature, for example at the boiliong point of the reaction mixture in an organic solvent or mixture of solvents, e.g. an alkanol and/or an aromatic hydrocarbon. A small amount of catalyst is added to accelerate the reaction. Example 1 describes the preparation of a compound of the formula IIIa and further compounds are listed in Table 1. These intermediates are novel and constitute an object of the invention. The condensates of formula IIIa are then reacted, in accordance with the first preparatory process, with a sulfonyl isocyanate of formula II, as described in Examples 9–11.

Scheme 2

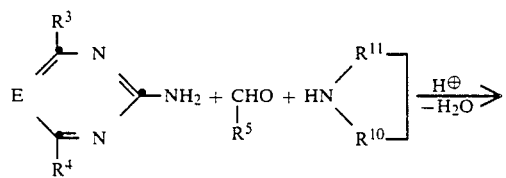

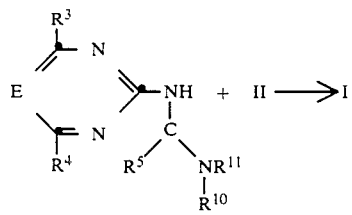

In this process also the 2-aminopyridine or 2-aminotriazine of formula VIII is reacted with a cyclic secondary amine. The reaction is conducted in the presence of a small amount of acid in an organic solovent. Examples 5–8 describe such reactions to give compounds of the formula IIIb. These compounds can then be further reacted with a sulfonyl isocyanate of formula II to give an urea of formula I, as described in Examples 12 and 13.

Scheme 3

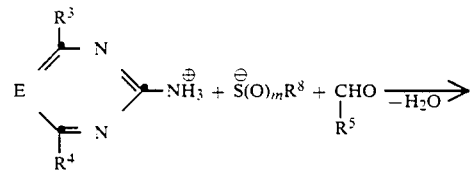

VIII

-continued
Scheme 3

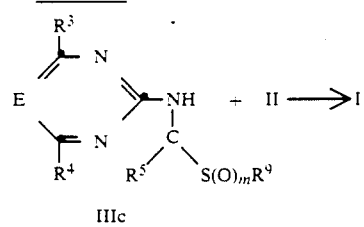

IIIc

The 2-aminopyrimidine or 2-aminotriazine of formula VIII and a sulfinic acid are charged to an organic solvent or diluent and the mixture is heated to give the aldehyde. The condensate can be precipitated by diluting the reaction mixture with water. Such a reaction is described in Example 2. Further compounds are listed in Table 2. The intermediates of formula IIIc likewise constitute an object of this invention. The further reaction of the compound of formula IIIc with a sulfonyl isocyanate of formula II to give the urea of formula I is performed in known manner.

A compound of formula IIIa can also be converted by oxidation into a compound of formula IIIc wherein n is 1 or 2.

The oxidation is carried out in an inert solvent or diluent in the temperature range from 0° C. to the boiling point of the reaction mixture. Suitable oxidising agents are hydrogen peroxide, an organic peracid such as perbenzoic acid or peracetic acid, or also potassium permanganate or chromium oxide. The duration of the oxidation and the amount of oxidising agent to be used depend on the desired oxidation step of the compound of formula IIIa.

Scheme 4

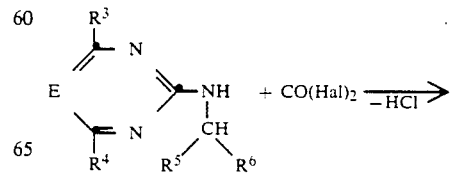

III

-continued

Scheme 4

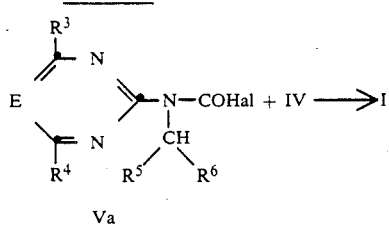

This scheme corresponds more or less to the above described second process for the preparation of the sulfonylureas of formula I, except that first a (2-pyrimidinyl)-N-methylcarbamoyl halide or N-(2-triazinyl)-N-methylcarbamoyl halide of the formula Va is prepared in a preliminary step, in an inert organic solvent, by condensing the compound of formula III with a carbonyl dihalide (phosgene), and then reacting the compound of formula Va with the sulfonamide of formula IV to give an urea of formula I.

Scheme 5

$$\text{IX} \xrightarrow{R^9S(O)_nCH_2Hal,\ \text{base}} I$$

A sulfonyl halide of formula IV is reacted with a methyl halide, in an inert organic solvent and in the presence of a base, to give an urea of formula I. The reaction takes place at room temperature and can be speeded up by heating briefly to the boiling point of the reaction mixture.

Scheme 6

$$\text{IX} + \underset{R^5}{\text{CHO}} + R^9\text{—SH} \xrightarrow[-H_2O]{H^\oplus} Ia$$

This schema is the same as scheme 1, except that a sulfonylurea of formula XI is used as starting material. This sulfonylurea is then reacted with an aldehyde and a mercaptan in an inert organic solvent or diluent and in the presence of a small amount of acid. The resultant sulfonylurea of formula Ia can be oxidized to give the corresponding sulfinyl or sulfonyl compound of formula Ib by an oxidation similar to that described after scheme III.

$$Ia \xrightarrow{ox.} Ib$$

Scheme 7

$$\text{IX} + \left[ \underset{R^5}{\text{CHO}} + \underset{R^{11}}{\text{HNR}^{10}} \right] \xrightarrow[-H_2O]{H^\oplus} I$$

This scheme is similar to scheme 2, except that the starting material employed is a sulfonylurea of formula IX, which is then reacted, in an inert solvent or diluent, with an aldehyde and a cyclic secondary amine, in the presence of a small amount of acid and at elevated temperature, to give an sulfonylurea of formula I.

The final products can be isolated by concentrating the reaction mixture and/or evaporating off the solvent, and purified by recrystallising or triturating the solid residue in solvents in which they are not readily soluble, e.g. in an ether, an aromatic hydrocarbon or a chlorinated hydrocarbon.

The compounds of formula I are stable compounds, and no protective measures are required for handling them.

When used at low rates of application, the compounds of formula I have good selective growth inhibiting and selective herbicidal properties which make them most suitable for use in crops of useful plants, especially in cereals, cotton, soybeans, maize and rice. In some cases damage is also caused to weeds which have only been controlled up to now with total herbicides.

The mode of action of these compounds is unusual. Many are translocatable, i.e. they are absorbed by the plant and transported to other parts of it where they then exert their action. Thus, for example, it is possible to damage perennial weeds to the roots by surface treatment. Compared with other herbicides and growth regulators, the novel compounds of the formula I are effective even when used at very low rates of application.

The compounds of formula I have in addition pronounced growth-regulating, especially growth-inhibiting, properties. The growth of both monocots and dicots is inhibited. Thus, for example, the compounds of formula I selectively inhibit the growth of leguminosae which are frequently planted as cover crops in tropical regions, so that, while soil erosion between cultivated plants is prevented, the cover crops cannot compete with the cultivated plants.

Inhibition of the vegetative growth of many cultivated plants permits more plants to be sown in a crop area, so that a higher yield may be obtained per unit of area. A further mechanism of yield increase using growth regulators reside in the fact that nutrients are able increasingly to promote flower formation and fruiting, whilst vegetative growth is inhibited.

At higher rates of application, all tested plants are so severely damaged in their development that they die.

The invention also relates to herbicidal and growth-regulating compositions which contain a novel compound of the formula I, and also to methods of controlling weeds pre- and postemergence and of inhibiting the growth of monocots and dicots, especially grasses, tropical cover crops and tobacco plant suckers.

The compounds of the formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulation in e.g. polymer substances. As with the nature of the compositions, the methods of applications, such as spraying, atomising, dusting, scattering or pouring, are chosen in accordance with the intended objectives and the prevailing circumstances.

The formulations, i.e. the compositions containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethylsulfoxide or dimethylformamide, as well as epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts or higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Exampls of alkylarylsulfonates are the sodium, calcium or triethylanolamine salts of dodecylbenzene sulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications:

"McCutcheon's Detergents and Emulsifiers Annual", MC Publishing Corp., Ridgewood, N.J., 1981; H. Stache, "Tensid-Taschenbuch", 2nd Edition, C. Hanser Verlag, Munich & Vienna, 1981; M. and J. Ash, "Encyclopedia of Surfactants", Vol. I-III, Chemical Publishing Co., New York, 1980-81.

The pesticidal compositions usually contain 0.1 to 95%, preferably 0.1 to 80%, of a compound of the formula I, 1 to 99.9%, of a solid or liquid adjuvant, and 0 to 25%, preferably 0.1 to 25%, of a surfactant.

Preferred formulations are composed in particular of the following constituents (%=percentage by weight):

| Emulsifiable concentrates | |
|---|---|
| active ingredient: | 1 to 20%, preferably 5 to 10% |
| surfactant: | 5 to 30%, preferably 10 to 20% |
| liquid carrier: | 50 to 94%, preferably 70 to 85% |
| Dusts | |
| active ingredient: | 0.1 to 10%, preferably 0.1 to 1% |
| solid carrier: | 99.9 to 90%, preferably 99.9 to 99% |
| Suspension concentrates | |
| active ingredient: | 5 to 75%, preferably 10 to 50% |
| water: | 94 to 25%, preferably 90 to 30% |
| surfactant: | 1 to 40%, preferably 2 to 30% |
| Wettable powders | |
| active ingredient: | 0.5 to 90%, preferably 1 to 80% |
| surfactant: | 0.5 to 20%, preferably 1 to 15% |
| solid carrier: | 5 to 95%, preferably 15 to 90% |
| Granulates | |
| active ingredient: | 0.5 to 30%, preferably 3 to 15% |
| solid carrier: | 99.5 to 70%, preferably 97 to 85%. |

Whereas commercial products will be preferably formulated as concentrates, the end user will normally employ dilute formulations. The formulations can be diluted to a concentration as low as 0.001% The rates of application are normally from 0.01 to 10 kg a.i./ha, preferably from 0.025 to 5 kg a.i./ha.

The compositions may also contain further ingredients such as stabilisers, antifoams, viscosity regulators, binders, tackifiers, as well as fertilisers and other compounds for obtaining special effects.

The invention is illustrated by the following Examples.

EXAMPLE 1

Preparation of 2-[(4-chlorophenylthio)methylamino]-4-methoxy-6-methylpyrimidine (intermediate)

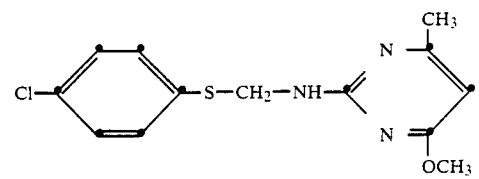

compound 1.02

A mixture of 13.99 g of 2-amino-4-methoxy-6-methylpyrimidine (0.1 mole), 14.8 g of 4-chlorothiophenol (0.1 mole), 9.4 g of aqueous 35% formaldehyde (0.11 mole) and 1 g of acetic acid are heated under reflux for 1 hour in 100 ml of methanol. The resultant solution is clarified by filtration, diluted with 150 ml of toluene and then the solvent is removed in a rotary evaporator. The residue crystallises after standing for some time. The melting point is 78°-82° after recrystallisation from hexane. The yield is 24 g (81% of theory).

The following compounds are prepared in accordance with this Example:

TABLE 1

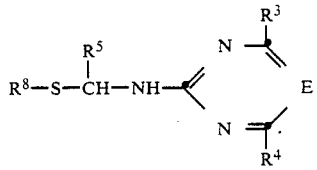

(IIIa)

| No. | $R^3$ | $R^4$ | $R^5$ | E | $R^8$ | m.p. (°C.) |
|---|---|---|---|---|---|---|
| 1.01 | $CH_3$ | $CH_3$ | H | CH | 4-chlorophenyl | 110-113° |
| 1.02 | $OCH_3$ | $CH_3$ | H | CH | 4-chlorophenyl | 78-82° |
| 1.03 | Cl | $OCH_3$ | H | CH | 4-chlorophenyl | 102-105° |
| 1.04 | $OCH_3$ | $OCH_3$ | H | CH | 4-chlorophenyl | 112-114° |
| 1.05 | $CH_3$ | $CH_3$ | H | CH | 4-fluorophenyl | 96-98° |
| 1.06 | $OCH_3$ | $CH_3$ | H | CH | 2,4,5-trichlorophenyl | 117-119° |
| 1.07 | $OCH_3$ | $CH_3$ | H | CH | 4-acetylaminophenyl | 182-183° |
| 1.08 | $CH_3$ | $CH_3$ | H | CH | β-naphthyl | 115-118° |
| 1.09 | $OCH_3$ | $CH_3$ | H | CH | β-naphthyl | 101-102° |
| 1.10 | $CH_3$ | $CH_3$ | H | CH | carbanilidomethyl | 128-130° |
| 1.11 | Cl | $OCH_3$ | H | CH | p-tolyl | 106-109° |
| 1.12 | $CH_3$ | $CH_3$ | H | CH | $-CH_2-COOH$ | 123-125° (dec.) |
| 1.13 | $CH_3$ | $OCH_3$ | H | CH | $-CH_2-COOH$ | 160-164° |
| 1.14 | $CH_3$ | $CH_3$ | H | CH | $-CH(CH_3)COOH$ | 141-145° |
| 1.15 | $CH_3$ | $CH_3$ | H | CH | $-CH_2CH_2-COOH$ | 150-153° |
| 1.16 | $CH_3$ | $CH_3$ | H | CH | $-CH_2-COOCH_3$ | 71-73° |
| 1.17 | $CH_3$ | $OCH_3$ | H | CH | $-CH_2-COOCH_3$ | 85-87° |
| 1.18 | $CH_3$ | $OCH_3$ | H | CH | N-phenylcarbamoyl-methyl | 161-163° |
| 1.19 | $OCH_3$ | $OCH_3$ | H | CH | 4-tolyl | 84-91° |
| 1.20 | $OCH_3$ | $CH_2-OCH_3$ | H | CH | 2,4,5-trichlorophenyl | 124-126° |
| 1.21 | $CH_3$ | $CH_3$ | $CH_3$ | CH | 2-carboxylphenyl | 162-163° |
| 1.22 | $CH_3$ | $CH_3$ | $C_3H_7(i)$ | CH | 2-carboxylphenyl | 138-141° |
| 1.23 | $CH_3$ | $CH_3$ | $-CH_2-Cl$ | CH | 2-carboxylphenyl | 220-222° (dec.) |
| 1.24 | $CH_3$ | $CH_3$ | $-COOH$ | CH | 2-carboxylphenyl | 180-182° |

TABLE 1-continued

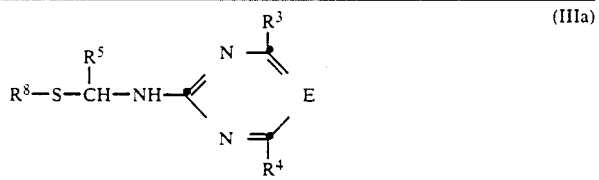

| No. | R³ | R⁴ | R⁵ | E | R⁸ | m.p. (°C.) |
|---|---|---|---|---|---|---|
| 1.25 | CH₃ | CH₃ | 2-Furyl | CH | 2-carboxylphenyl | 169-171° (dec.) |
| 1.26 | CH₃ | CH₃ | 4-Chlorphenyl | CH | 2-carboxylphenyl | 193-195° (dec.) |
| 1.27 | CH₃ | CH₃ | H | CH | 2-carboxylphenyl | 226-228° (dec.) |

EXAMPLE 2

Preparation of 4-dimethylamino-6-methoxy-2-(4-tolylsulfonyl)methylamino-1,3,5-triazine

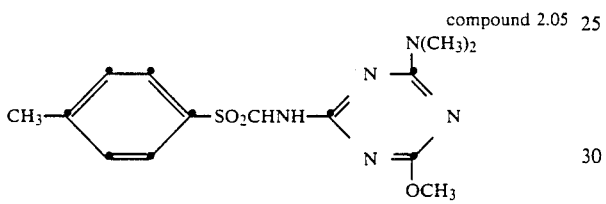

compound 2.05

8.5 g (0.05 mole) of 2-amino-4-dimethylamino-6-methoxy-1,3,5-triazine and 9.1 g (0.05 mole) of toluene-4-sulfinic acid, sodium salt, are suspended in 100 ml of methanol and to the stirred suspension are added, in succession, 4.8 g (0.05 mole) of methanesulfonic acid and 4.7 g (0.055 mole) of aqueous 35% formaldehyde. The batch is then stirred for 30 minutes at room temperature and then for another 90 minutes under reflux. After cooling, the mixture is diluted with 1 liter of water and the crystalline precipitate is filtered with suction and dried. Melting point: 188°-190° C. Yield: 10 g (59% of theory).

EXAMPLE 3

Preparation of 4,6-dimethyl-2-(4-tolylsulfonylmethylamino)pyrimidine

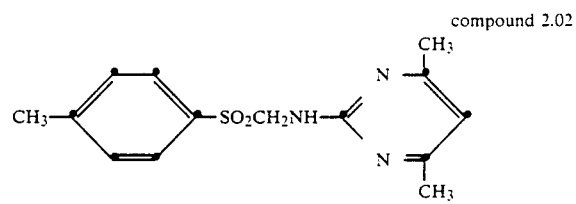

compound 2.02

12.7 g (0.1 mole) of 2-amino-4,6-dimethylpyrimidine are suspended in 200 ml of water and then 9.7 g (0.1 mole) of methanesulfonic acid are stirred in to form a solution. To the stirred solution are added, in succession, 18.22 g (0.1 mole) of toluene-3-sulfonic acid, sodium salt, and 9.4 g (0.11 mole) of aqueous 35% formaldehyde. The mixture is stirred for 2 hours at room temperature and for another 30 minute at 90° C. The colourless precipitate is filtered with suction after cooling and dried. Melting point: 191°-194° C. Yield: 25 g (86% of theory).

The following compounds are obtained in accordance with Examples 2 and 3:

TABLE 2

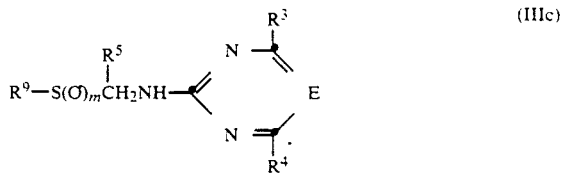

| No. | R³ | R⁴ | R⁵ | m | E | R⁹ | m.p. (°C.) |
|---|---|---|---|---|---|---|---|
| 2.01 | CH₃ | CH₃ | H | 2 | CH | CH₃ | 145-148 |
| 2.02 | CH₃ | CH₃ | H | 2 | CH | p-tolyl | 191-194° |
| 2.03 | OCH₃ | CH₃ | H | 2 | CH | p-tolyl | 136-138° |
| 2.04 | OCHF₂ | CH₃ | H | 2 | CH | p-tolyl | 165-166° |
| 2.05 | N(CH₃)₂ | OCH₃ | H | 2 | N | p-tolyl | 188-190° |
| 2.06 | OCH₃ | OCH₃ | H | 2 | CH | p-tolyl | 135-140° |
| 2.07 | OCH₃ | CH₂COH₃ | H | 2 | CH | p-tolyl | 142-144° |
| 2.08 | Cl | OCH₃ | H | 2 | CH | p-tolyl | |
| 2.09 | Cl | CH₃ | H | 2 | CH | p-tolyl | |
| 2.10 | CH₃ | CH₃ | H | 2 | CH | 4-chlorophenyl | 178-180° |
| 2.11 | OCH₃ | CH₃ | H | 2 | CH | 4-chlorophenyl | |
| 2.12 | CH₃ | CH₃ | H | 2 | CH | 4-bromophenyl | 184-186° |
| 2.13 | CH₃ | OCH₃ | H | 2 | CH | CH₃ | 149-150° |
| 2.14 | CH₃ | CH₃ | H | 2 | CH | benzyl | 154-159° |
| 2.15 | CH₃ | OCH₃ | H | 2 | CH | β-naphthyl | 167-169° |

TABLE 2-continued

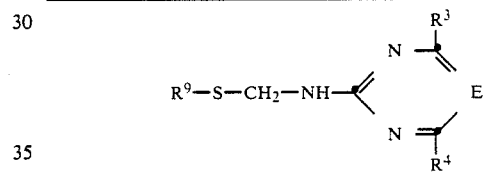

| No. | $R^3$ | $R^4$ | $R^5$ | m | E | $R^9$ | m.p. (°C.) |
|---|---|---|---|---|---|---|---|
| 2.16 | $CH_3$ | $CH_3$ | $CH_3$ | 2 | CH | p-tolyl | 125–127° |
| 2.17 | $CH_3$ | $CH_3$ | $C_3H_7i$ | 2 | CH | p-tolyl | 116–118° |
| 2.18 | $OCH_3$ | $OCH_3$ | H | 2 | CH | $CH_3$ | 149–151° |
| 2.19 | $OCH_3$ | $OCH_3$ | H | 2 | CH | $C_2H_5$ | 145–147° |
| 2.20 | $OCH_3$ | $OCH_3$ | H | 2 | CH | $n-C_3H_7$ | 117–120° |
| 2.21 | $OCH_3$ | $OCH_3$ | H | 2 | CH | benzyl | 138–139° |
| 2.22 | $OCH_3$ | $OCH_3$ | H | 2 | CH | 2-methoxy-carbonylbenzyl | 135–136° |
| 2.23 | $OCH_3$ | $OCH_3$ | H | 2 | CH | phenyl | 135–139° |
| 2.24 | $OCH_3$ | $OCH_3$ | H | 2 | CH | 2-difluoro-methoxyphenyl | 137–138° |
| 2.25 | $OCH_3$ | $OCH_3$ | H | 2 | CH | 2,4,6-tri-methylphenyl | 131–133° |
| 2.26 | $OCH_3$ | $OCH_3$ | H | 2 | CH | 4-bromophenyl | 137–138° |
| 2.27 | $OCH_3$ | $OCH_3$ | H | 2 | CH | 4-chlorophenyl | 140–141° |
| 2.28 | $OCH_3$ | $OCH_3$ | H | 2 | CH | β-naphthyl | 139–140° |
| 2.29 | $OCHF_2$ | $CH_3$ | H | 2 | CH | $CH_3$ | 162–163° (dec.) |
| 2.30 | $N(CH_3)_2$ | $OCH_3$ | H | 2 | CH | $CH_3$ | 184–187° (dec.) |

EXAMPLE 4

Preparation of 4,6-dimethyl-2-(morpholin-4-ylthiocarbonylthiomethylamino)pyrimidine

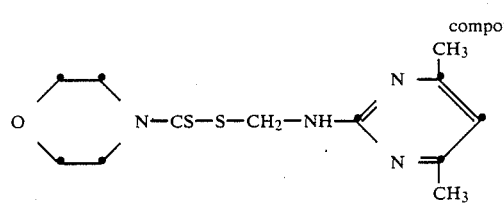

6.6 g (0.1 mole) of 85% potassium hydroxide and 8.9 g (0.1 mole) of morpholine are dissolved in 200 ml of water and, with cooling, 7.7 g (0.1 mole) of carbon disulfide are added. The mixture is stirred until a yellowish homogeneous solution is obtained. With cooling and stirring, 9.4 g (0.11 mole) of aqueous 35% formaldehyde and a solution of 12.7 g (0.1 mole) of 2-amino-4,6-dimethylpyrimidine and 9.7 g (0.1 mole) of methanesulfonic acid in 50 ml of water are added in succession. The reaction mixture is further stirred at room temperature, whereupon first an oil precipitates, which crystallises after a short time. After 24 hours the batch is diluted with 1 liter of water and the crystalline precipitate is filtered with suction and dried, affording 24 g (80% of theory) of the title compound with a melting point of 119°–121° C.

The following compounds are prepared in accordance with Example 4:

TABLE 3

| No. | $R^3$ | $R^4$ | E | $R^9$ | m.p. (°C.) |
|---|---|---|---|---|---|
| 3.01 | $CH_3$ | $CH_3$ | CH | pyrrolidinothiocarbonyl | 116–118° |
| 3.02 | $CH_3$ | $CH_3$ | CH | morpholinothiocarbonyl | 119–121° |
| 3.03 | Cl | $OCH_3$ | CH | pyrrolidinothiocarbonyl | 136–139° |
| 3.04 | $CH_3$ | $CH_3$ | CH | azepinylthiocarbonyl | 90–92° |
| 3.05 | $CH_3$ | $CH_3$ | CH | methoxythiocarbonyl | |
| 3.06 | $CH_3$ | $CH_3$ | CH | dimethylthiocarbamoyl | 105–115° |
| 3.07 | $CH_3$ | $CH_3$ | CH | acetyl | |
| 3.08 | $CH_3$ | $CH_3$ | CH | benzoyl | >110° (dec.) |
| 3.09 | $OCHF_2$ | $CH_3$ | CH | benzoyl | 125–128° (dec.) |
| 3.10 | $CH_3$ | $OCH_3$ | CH | benzoyl | 107–109° |

EXAMPLE 5

Preparation of 4-methoxy-6-methyl-2-(1,2,4-triazol-1-ylmethylamino)-pyrimidine

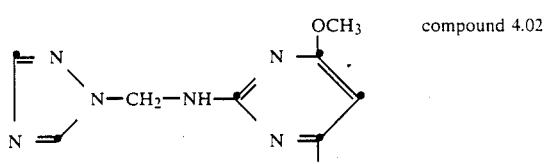

With stirring, a mixture of 13.9 g (0.1 mole) of 2-amino-4-methoxy-6-methylpyrimidine, 7 g (0.1 mole) of 1,2,4-triazole, 9.4 g (0.11 mole) of aqueous 35% formaldehyde and 1 g of acetic acid in 100 ml of methanol is refluxed for 1½ hours. First a clear solution forms, from which the reaction product precipitates in crystalline form after a time. After the reaction mixture has cooled, the crystalline title compound is filtered with suction and dried. Yield: 14 g. Melting point: 191°-193° C.

EXAMPLE 6

Preparation of 2-[(2,6-dichlorophenyl)-(1,2,4-triazol-1-yl)methyl]-amino-4,6-dimethylpyrimidine

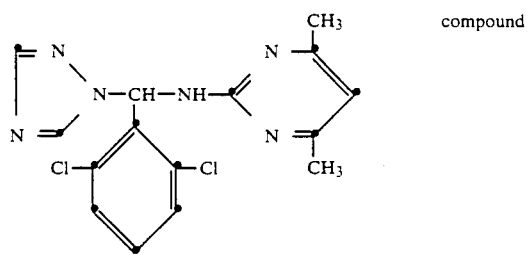

compound

With stirring, a mixture of 6.3 g (0.05 mole) of 2-amino-4,6-dimethylpyrimidine, 8.8 g (0.05 mole) of 2,6-dichlorobenzaldehyde, 3.5 g (0.105 mole) of 1,2,4-triazole and 1 g of acetic acid in 50 ml of methanol is heated under reflux for 2 hours. The resultant clear yellowish solution is concentrated in a rotary evaporator and the residue is crystallised from methanol, affording 6 g (34% of theory) of the title compound, which undergoes conversion at 140°-145° C. and then melts at 158°-159° C.

EXAMPLE 7

Preparation of 2-(benztriazol-1-ylmethylamino)-4-dimethylamino-6-methoxy-1,3,5-triazine

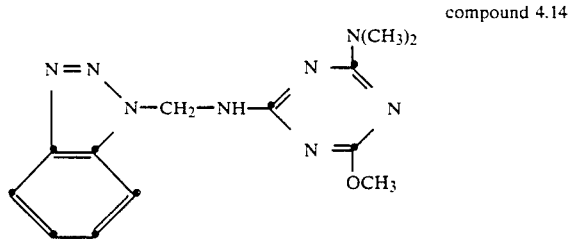

compound 4.14

With stirring, a mixture of 16.9 g (0.1 mole) of 2-amino-4-dimethylamino-6-methoxy-1,3,5-triazine, 12 g (0.1 mole) of benztriazole, 9.4 g (0.11 mole) of aqueous 35% formaldehyde and 1 g of acetic acid in 100 ml of ethanol is heated under reflux for 2 hours. The still hot solution is clarified by filtration and crystals of the title compound precipitate from the cooled solution. The precipitate is filtered with suction and dried, affording 25 g (83% of theory) of crystalline product with a melting point of 222°-224° C.

EXAMPLE 8

Preparation of 4,6-dimethyl-2-[2-methylbenzimidizol-1-yl)methylamino]pyrimidine

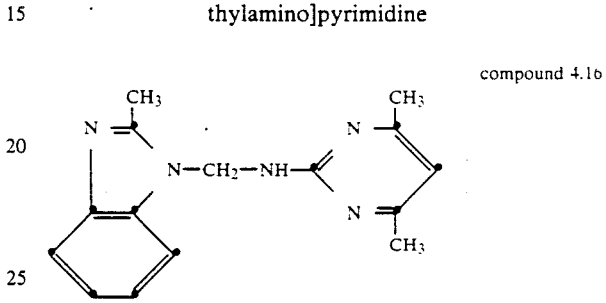

compound 4.16

With stirring, a mixture of 6.3 g (0.05 mole) of 2-amino-4,6-di-methylpyrimidne, 6.7 g (0.05 mole), 4.7 g (0.0055 mole) of aqueous 35% formaldehyde and 1 g of acetic acid in 50 ml of methanol is heated under reflux for 1½ hours. To the resultant colourless solution are added 150 ml of toluene and the solvent is then removed in a rotary evaporator. The precipitated crystalline residue is recrystallised from ethyl acetete/methanol, affording 10 g (70% of theory) of the title compound which melts at 207°-212° C.

The following compounds are obtained by procedures analogous to those described in Examples 5 to 8:

TABLE 4

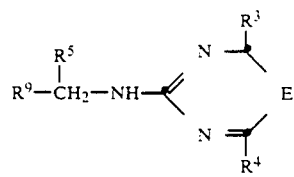

| No. | R³ | R⁴ | R⁵ | E | R⁹ | m.p. (°C.) |
|---|---|---|---|---|---|---|
| 4.01 | CH₃ | CH₃ | H | CH | 1,2,4-triazol 1-yl | 162–164° |
| 4.02 | OCH₃ | CH₃ | H | CH | 1,2,4-triazol-1-yl | 191–193° |
| 4.03 | OCH₃ | OCH₃ | H | CH | 1,2,4-triazol-1-yl | 166–168° |
| 4.04 | OCHF₂ | CH₃ | H | CH | 1,2,4-triazol-1-yl | 187–189° |
| 4.05 | OCH₃ | CH₂OCH₃ | H | CH | 1,2,4-triazol-1-yl | 180–181° |

TABLE 4-continued

[Structure: $R^9-CH_2-NH-$ group attached to a ring with $R^3$, $R^4$, $R^5$, E substituents]

| No. | | | | | | m.p. (°C.) |
|---|---|---|---|---|---|---|
| 4.06 | Cl | OCH₃ | H | CH | 1,2,4-triazol-1-yl | 157–159° |
| 4.07 | OCH₃ | OCH₃ | H | N | 1,2,4-triazol-1-yl | 197–200° (dec.) |
| 4.08 | N(CH₃)₂ | OCH₃ | H | N | 1,2,4-triazol-1-yl | 206–208° |
| 4.09 | CH₃ | CH₃ | H | CH | benztriazol-1-yl | 204–205° |
| 4.10 | OCH₃ | CH₃ | H | CH | benztriazol-1-yl | 165–167° |
| 4.11 | OCH₃ | OCH₃ | H | CH | benztriazol-1-yl | 168–170° |
| 4.12 | OCH₃ | CH₂OCH₃ | H | CH | benztriazol-1-yl | 132–134° |
| 4.13 | OCHF₂ | CH₃ | H | CH | benztriazol-1-yl | 142–144° |

| No. | $R^3$ | $R^4$ | $R^5$ | E | $R^8$ | m.p. (°C.) |
|---|---|---|---|---|---|---|
| 4.14 | CH₃ | OCH₃ | H | CH | 5(6)-nitro-benztriazol-1-yl | 190–193°* |
| 4.15 | OCH₃ | OCH₃ | H | CH | 5(6)-nitro-benztriazol-1-yl | 173–175°* |
| 4.16 | CH₃ | OCH₃ | H | CH | 5(6)-chlorobenztriazol-1-yl | 156–168°* |
| 4.17 | N(CH₃)₂ | OCH₃ | H | N | benztriazol-1-yl | 222–224° |
| 4.18 | CH₃ | CH₃ | H | CH | 4aH-carbazol-1-yl | 153–155° |
| 4.19 | CH₃ | CH₃ | H | CH | 2-methyl-benzimidazol-1-yl | 207–212° |
| 4.20 | CH₃ | CH₃ | H | CH | 2,3-dimethylindol-1-yl | |
| 4.21 | CH₃ | OCH₃ | H | N | 2,3-dimethylindol-1-yl | |
| 4.22 | OCHF₂ | CH₃ | H | CH | 2,3-dimethylindol-1-yl | |
| 4.23 | CH₃ | CH₃ | H | CH | 2,4,5-tribromimidazol-1-yl | |
| 4.24 | CH₃ | CH₃ | H | CH | 2,4,5-tribromimidazol-1-yl | |
| 4.25 | N(CH₃)₂ | OCH₃ | H | N | 2,4,5-tribromimidazol-1-yl | |
| 4.26 | CH₃ | OCH₃ | H | CH | pyrazol-1-yl | |
| 4.27 | OCHF₂ | CH₃ | H | CH | pyrazol-1-yl | |
| 4.28 | Cl | OCH₃ | H | N | pyrazol-1-yl | |
| 4.29 | CH₃ | OCH₃ | CH₃ | CH | 1,2,4-triazol-1-yl | |

*mixture of isomers

EXAMPLE 9

Preparation of N-2-chlorophenylsulfonyl-N'-(4-chlorophenylthiomethyl)-N'-(4,6-dimethylpyrimidin-2-yl)urea

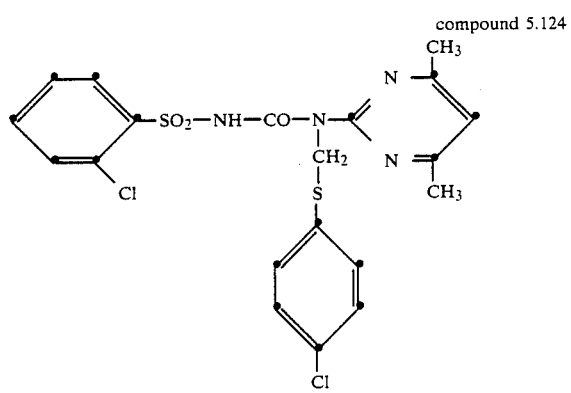

compound 5.124

7.5 g (0.027 mole) of 2-(4-chlorophenylthio)methylamino-4,6-dimethylpyrimidine are suspended in 50 ml of absolute acetonitrile and then 5.8 g (0.027 mole) of 2-chlorophenylisocyanate are added. The batch is stirred for 24 hours at room temperature, then the solvent is removed in a rotary evaporator and the residue is taken up in ethyl acetate. The solution is purified by chromatography through a column of silica gel eluted with ethyl acetetate/cyclohexane. The title compound precipitates in crystalline form after removal of the solvent by evaporation. Yield: 6.0 g (45% of theory). Melting point: 132°–135° C.

EXAMPLE 10

Preparation of N-(2-difluoromethoxyphenylsulfonyl)-N'-(p-tolylulfonylmethyl)-N'-(-4-difluoromethoxy-6-methylpyrimidin-2-yl)urea

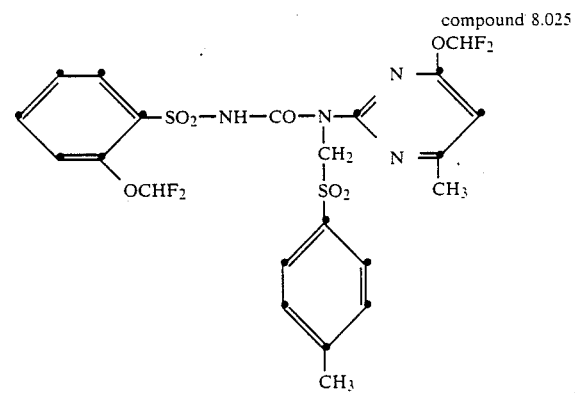

compound 8.025

5.5 g (0.016 mole) of 4-difluoromethoxy-6-methyl-2-p-tolylsulfonylmethylaminopyrimidine are suspended in 50 ml of absolute dioxan and then 4 g (0.016 mole) of 2-difluoromethoxyphenylisocyanate are stirred into the suspension. Stirring is continued for 3 hours at room temperature to give a clear solution, which is concentrated in a rotary evaporator. The residue crystallises spontaneously when stirred in ether. The crystals are filtered with suction and dried, affording 8 g (84% of theory) of crystalline title compound with a melting point of 159°–164° C. (dec.).

EXAMPLE 11

Preparation of N-(2-chlorophenylsulfonyl)-N'-(pyrrolidinothiocarbonylthiomethyl)-N'-(4,6-dimethylpyrimidin-2-yl)urea

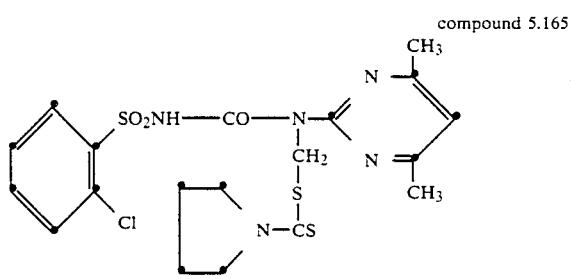

compound 5.165

5.5 g (0.019 mole) of 2-(pyrrolidinothiocarbonylthiomethyl)-4,6-dimethylpyrimidine are suspended in 30 ml of absolute acetonitrile and then 4.3 g (0.019 mole) of 2-chlorophenylsulfonylisocyanate are stirred into the suspension. The batch is stirred for 5 hours at room temperature to give first a clear solution from which the final product precipitates after a time. The reaction mixture is cooled and then filtered with suction, affording 6 g (63% of theory) of title compound which melts at 131°–133° C. with decomposition.

EXAMPLE 12

Preparation of N-(2-chlorophenylsulfonyl)-N'-(1,2,4-triazol-1-ylmethyl)-N'-(4,6-dimethylpyrimidin-2-yl)urea

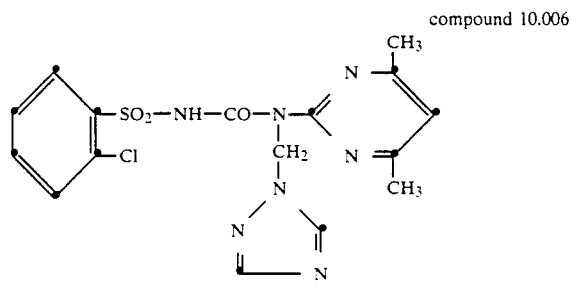

compound 10.006

4 g (0.019 mole) of 2-(1,2,4-triazol-1-ylmethylamino)-4,6-dimethylpyrimidine are suspended in 100 ml of absolute acetonitrile and then 4.3 g (0.019 mole) of 2-chlorophenylsulfonylisocyanate are stirred into the suspension. The batch is stirred for 24 hours at room temperature and the resultant solution is finally concentrated in a rotary evaporator. Crystals of the title compound precipitate and are recrystallised from ethyl acetate, affording 5 g (62% of theory) of the above urea, which melts at 152°–157° C.

EXAMPLE 13

Preparation of N-(2-(2-methoxycarbonylphenylsulfonyl-N'-(benztriazol-1-methyl)-N'-4,6-dimethylpyrimidin-2-yl)urea

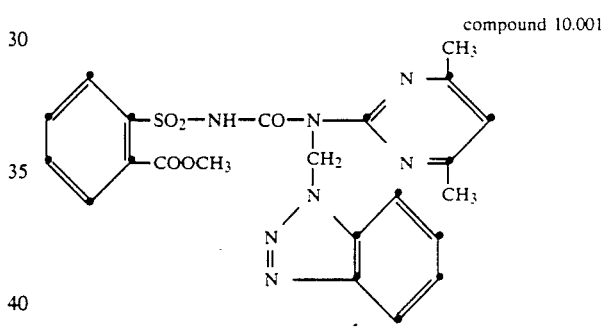

compound 10.001

6.5 g (0.026 mole) of 2-(benztriazol-1-ylmethylaminop)-4,6-dimethylpyrimidine are suspended in 70 ml of absolute dioxan and then 6.2 g (0.026 mole) of 2-methoxycarbonylphenylsulfonylisocyanate are stirred into the suspension. The batch is stirred for 24 hours at room temperature and the resultant solution is concentrated in a rotary evaporator. The residue is taken up in ethyl acetate and the solution is purified by chromatography through a column of silica gel eluted with ethyl acetate/cyclohexane. The solvent is evaporated off, affording 7.5 g (58% of theory) of crystalline title compound with a melting point of 178°–180° C. (dec.).

The following compounds are prepared by procedures analogous to those described in Examples 9–13:

TABLE 5

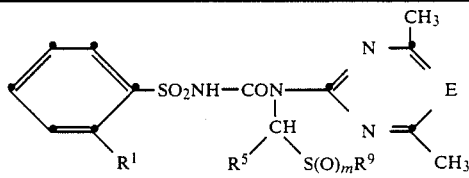

| No | R¹ | R⁵ | m | R⁹ | E | m.p. (°C.) |
|---|---|---|---|---|---|---|
| 5.001 | COOCH₃ | H | 2 | p-tolyl | CH | 159–160° |
| 5.002 | COOCH₃ | H | 0 | p-tolyl | CH | |
| 5.003 | COOCH₃ | H | 2 | 4-chlorophenyl | CH | |
| 5.004 | COOCH₃ | H | 0 | 4-chlorophenyl | CH | 141–144° |
| 5.005 | COOCH₃ | H | 0 | acetyl | CH | |
| 5.006 | COOCH₃ | H | 0 | benzoyl | CH | |
| 5.007 | COOCH₃ | H | 2 | CH₃ | CH | 130–135° (dec.) |
| 5.008 | COOCH₃ | H | 2 | CH₂CH₂CH₂CH₃ | CH | |
| 5.009 | COOCH₃ | H | 2 | CH(CH₃)₂ | CH | |
| 5.010 | COOCH₃ | H | 2 | benzyl | CH | |
| 5.011 | COOCH₃ | H | 2 | phenyl | CH | |
| 5.012 | COOCH₃ | H | 0 | phenyl | CH | |
| 5.013 | COOCH₃ | H | 2 | 4-bromophenyl | CH | |
| 5.014 | COOCH₃ | H | 0 | 4-bromophenyl | CH | |
| 5.015 | COOCH₃ | H | 2 | 2-chlorophenyl | CH | |
| 5.016 | COOCH₃ | H | 0 | 2-chlorophenyl | CH | |
| 5.017 | COOCH₃ | H | 0 | CH₃ | CH | |
| 5.018 | COOCH₃ | H | 0 | CH₂CH₂CH₂CH₃ | CH | |
| 5.019 | COOCH₃ | H | 0 | CH(CH₃)₂ | CH | |
| 5.020 | COOCH₃ | H | 0 | benzyl | CH | |
| 5.021 | COOCH₃ | H | 2 | β-naphthyl | CH | |
| 5.022 | COOCH₃ | H | 0 | β-naphthyl | CH | 178–183° (dec.) |
| 5.023 | COOCH₃ | H | 2 | 1,2,4-trichlorophenyl | CH | |
| 5.024 | COOCH₃ | H | 0 | 1,2,4-trichlorophenyl | CH | |
| 5.025 | COOCH₃ | H | 2 | α-naphthyl | CH | |
| 5.026 | COOCH₃ | H | 2 | α-naphthyl | CH | |
| 5.027 | COOCH₃ | H | 0 | —CH₂COOCH₃ | CH | |
| 5.028 | COOCH₃ | H | 2 | 4-fluorophenyl | CH | |
| 5.029 | COOCH₃ | H | 0 | 4-fluorophenyl | CH | |
| 5.030 | COOCH₃ | H | 0 | 4-nitrophenyl | CH | |
| 5.031 | COOCH₃ | H | 0 | 4-nitrophenyl | CH | |
| 5.032 | COOCH₃ | H | 2 | 2-nitrophenyl | CH | |
| 5.033 | COOCH₃ | H | 0 | 2-nitrophenyl | CH | |
| 5.034 | COOCH₃ | H | 2 | 2-trifluoromethyl | CH | |
| 5.035 | COOCH₃ | H | 0 | 2-trifluoromethyl | CH | |
| 5.036 | COOCH₃ | H | 2 | 4-methoxyphenyl | CH | |
| 5.037 | COOCH₃ | H | 0 | 4-methoxyphenyl | CH | |
| 5.038 | COOCH₃ | H | 2 | 2-methoxyphenyl | CH | |
| 5.039 | COOCH₃ | H | 0 | 2-methoxyphenyl | CH | |
| 5.040 | COOCH₃ | H | 2 | 2,4,6-trimethylphenyl | CH | |
| 5.041 | COOCH₃ | H | 0 | 2,4,6-trimethylphenyl | CH | |
| 5.042 | COOCH₃ | H | 0 | CS—N(CH₃)₂ | CH | |
| 5.043 | COOCH₃ | H | 0 | CSN(CH₂CH₃)₂ | CH | |
| 5.044 | COOCH₃ | H | 0 | CSN(CH₂CH₃)₂ | CH | |
| 5.045 | COOCH₃ | H | 0 | pyrrolidinothiocarbonyl | CH | |
| 5.046 | COOCH₃ | H | 0 | piperidinothiocarbonyl | CH | |
| 5.047 | COOCH₃ | H | 0 | anilidoacetyl | CH | |
| 5.048 | COOCH₃ | H | 0 | 2,4-dichlorophenyl | CH | |
| 5.049 | COOCH₃ | H | 2 | 2,4-dichlorophenyl | CH | |
| 5.050 | COOCH₃ | H | 0 | CH₂COOH | CH | |
| 5.051 | COOCH₃ | H | 0 | CH₂COO CH₃ | CH | 154–156° |
| 5.052 | COOCH₃ | H | 0 | CH₂CON(CH₃)₂ | CH | |
| 5.053 | COOCH₃ | H | 0 | 4-chlorophenyl | N | |
| 5.054 | COOCH₃ | H | 0 | p-tolyl | N | |
| 5.055 | COOCH₃ | furyl-2- | 0 | 2-hydroxycarbonylphenyl | CH | |
| 5.056 | COOCH₃ | furyl-2- | 0 | 2-methoxycarbonylphenyl | CH | |
| 5.057 | COOCH₃ | furyl-2- | 0 | phenyl | CH | |
| 5.058 | COOCH₃ | 4-chlorophenyl | 0 | 2-hydroxycarbonylphenyl | CH | |
| 5.059 | COOCH₃ | 4-chlorophenyl | 0 | phenyl | CH | |
| 5.060 | COOCH₃ | CH₃ | 0 | 4-chlorophenyl | CH | |
| 5.061 | OCHF₂ | H | 2 | p-tolyl | CH | 152–157° (dec.) |
| 5.062 | OCHF₂ | H | 0 | p-tolyl | CH | |

TABLE 5-continued

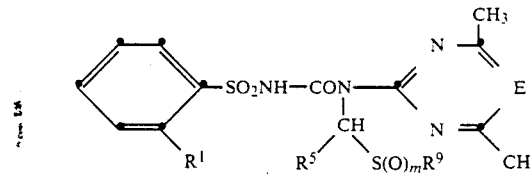

| No | R¹ | R⁵ | m | R⁹ | E | m.p. (°C.) |
|---|---|---|---|---|---|---|
| 5.063 | OCHF₂ | H | 2 | 4-chlorophenyl | CH | |
| 5.064 | OCHF₂ | H | 0 | 4-chlorophenyl | CH | 109–111° |
| 5.065 | OCHF₂ | H | 0 | acetyl | CH | |
| 5.066 | OCHF₂ | H | 0 | benzoyl | CH | 155–158° dec. |
| 5.067 | OCHF₂ | H | 2 | CH₃ | CH | |
| 5.068 | OCHF₂ | H | 2 | CH₂CH₂CH₂CH₃ | CH | |
| 5.069 | OCHF₂ | H | 2 | CH(CH₃)₂ | CH | |
| 5.070 | OCHF₂ | H | 2 | benzyl | CH | |
| 5.071 | OCHF₂ | H | 2 | phenyl | CH | |
| 5.072 | OCHF₂ | H | 0 | phenyl | CH | |
| 5.073 | OCHF₂ | H | 2 | 4-bromophenyl | CH | |
| 5.074 | OCHF₂ | H | 0 | 4-bromophenyl | CH | |
| 5.075 | OCHF₂ | H | 2 | 2-chlorophenyl | CH | |
| 5.076 | OCHF₂ | H | 0 | 2-chlorophenyl | CH | |
| 5.077 | OCHF₂ | H | 0 | CH₃ | CH | |
| 5.078 | OCHF₂ | H | 0 | CH₂CH₂CH₂CH₃ | CH | |
| 5.079 | OCHF₂ | H | 0 | CH(CH₃)₂ | CH | |
| 5.080 | OCHF₂ | H | 0 | benzyl | CH | |
| 5.081 | OCHF₂ | H | 2 | β-naphthyl | CH | |
| 5.082 | OCHF₂ | H | 0 | β-naphthyl | CH | 162–164° |
| 5.083 | OCHF₂ | H | 2 | 1,2,4-trichlorophenyl | CH | |
| 5.084 | OCHF₂ | H | 0 | 1,2,4-trichlorophenyl | CH | |
| 5.085 | OCHF₂ | H | 2 | α-naphthyl | CH | |
| 5.086 | OCHF₂ | H | 2 | α-naphthyl | CH | |
| 5.087 | OCHF₂ | H | 0 | —CH₂COOCH₃ | CH | |
| 5.088 | OCHF₂ | H | 2 | 4-fluorophenyl | CH | |
| 5.089 | OCHF₂ | H | 0 | 4-fluorophenyl | CH | 125–127° |
| 5.090 | OCHF₂ | H | 0 | 4-nitrophenyl | CH | |
| 5.091 | OCHF₂ | H | 0 | 4-nitrophenyl | CH | |
| 5.092 | OCHF₂ | H | 2 | 2-nitrophenyl | CH | |
| 5.093 | OCHF₂ | H | 0 | 2-nitrophenyl | CH | |
| 5.094 | OCHF₂ | H | 2 | 2-trifluoromethyl | CH | |
| 5.095 | OCHF₂ | H | 0 | 2-trifluoromethyl | CH | |
| 5.096 | OCHF₂ | H | 2 | 4-methoxyphenyl | CH | |
| 5.097 | OCHF₂ | H | 0 | 4-methoxyphenyl | CH | |
| 5.098 | OCHF₂ | H | 2 | 2-methoxyphenyl | CH | |
| 5.099 | OCHF₂ | H | 0 | 2-methoxyphenyl | CH | |
| 5.100 | OCHF₂ | H | 2 | 2,4,6-trimethylphenyl | CH | |
| 5.101 | OCHF₂ | H | 0 | 2,4,6-trimethylphenyl | CH | |
| 5.102 | OCHF₂ | H | 0 | CS—N(CH₃)₂ | CH | 139–142° dec. |
| 5.103 | OCHF₂ | H | 0 | CSN(CH₂CH₃)₂ | CH | |
| 5.104 | OCHF₂ | H | 0 | CSN(CH₂CH₃)₂ | CH | |
| 5.105 | OCHF₂ | H | 0 | pyrrolidinothiocarbonyl | CH | 136–139° dec. |
| 5.106 | OCHF₂ | H | 0 | piperidinothiocarbonyl | CH | |
| 5.107 | OCHF₂ | H | 0 | N-phenylcarbamoylmethyl | CH | 110–112° |
| 5.108 | OCHF₂ | H | 0 | 2,4-dichlorophenyl | CH | |
| 5.109 | OCHF₂ | H | 2 | 2,4-dichlorophenyl | CH | |
| 5.110 | OCHF₂ | H | 0 | CH₂COOH | CH | |
| 5.111 | OCHF₂ | H | 0 | CH₂COO CH₃ | CH | |
| 5.112 | OCHF₂ | H | 0 | CH₂CON(CH₃)₂ | CH | |
| 5.113 | OCHF₂ | H | 0 | 4-chlorophenyl | N | |
| 5.114 | OCHF₂ | H | 0 | p-tolyl | N | |
| 5.115 | OCHF₂ | Furyl-2- | 0 | 2-hydroxycarbonylphenyl | CH | |
| 5.116 | OCHF₂ | Furyl-2- | 0 | 2-methoxycarbonylphenyl | CH | |
| 5.117 | OCHF₂ | Furyl-2- | 0 | phenyl | CH | |
| 5.118 | OCHF₂ | 4-Chlorphenyl | 0 | 2-hydroxycarbonylphenyl | CH | |
| 5.119 | OCHF₂ | 4-Chlorphenyl | 0 | phenyl | CH | |
| 5.120 | OCHF₂ | CH₃ | 0 | 4-chlorophenyl | CH | |
| 5.121 | Cl | H | 2 | p-tolyl | CH | 153–155° |

TABLE 5-continued

[Structure: phenyl-SO₂NH—CON(CH(R⁵)S(O)ₘR⁹)— connected to a 6-membered ring with two N atoms, each bearing CH₃ groups, and E; R¹ on phenyl]

| No | R¹ | R⁵ | m | R⁹ | E | m.p. (°C.) |
|---|---|---|---|---|---|---|
| 5.122 | Cl | H | 0 | p-tolyl | CH | 86–88 (dec.) |
| 5.123 | Cl | H | 2 | 4-chlorophenyl | CH | |
| 5.124 | Cl | H | 0 | 4-chlorophenyl | CH | 132–135° dec. |
| 5.125 | Cl | H | 0 | acetyl | CH | |
| 5.126 | Cl | H | 0 | benzoyl | CH | |
| 5.127 | Cl | H | 2 | CH₃ | CH | |
| 5.128 | Cl | H | 2 | CH₂CH₂CH₂CH₃ | CH | |
| 5.129 | Cl | H | 2 | CH(CH₃)₂ | CH | |
| 5.130 | Cl | H | 2 | benzyl | CH | 146–147° (dec.) |
| 5.131 | Cl | H | 2 | phenyl | CH | |
| 5.132 | Cl | H | 0 | phenyl | CH | |
| 5.133 | Cl | H | 2 | 4-bromophenyl | CH | 150–153° (dec.) |
| 5.134 | Cl | H | 0 | 4-bromophenyl | CH | |
| 5.135 | Cl | H | 2 | 2-chlorophenyl | CH | |
| 5.136 | Cl | H | 0 | 2-chlorophenyl | CH | |
| 5.137 | Cl | H | 0 | CH₃ | CH | |
| 5.138 | Cl | H | 0 | CH₂CH₂CH₂CH₃ | CH | |
| 5.139 | Cl | H | 0 | CH(CH₃)₂ | CH | |
| 5.140 | Cl | H | 0 | benzyl | CH | |
| 5.141 | Cl | H | 2 | β-naphthyl | CH | |
| 5.142 | Cl | H | 0 | β-naphthyl | CH | 156–158° |
| 5.143 | Cl | H | 2 | 1,2,4-trichlorophenyl | CH | |
| 5.144 | Cl | H | 0 | 1,2,4-trichlorophenyl | CH | |
| 5.145 | Cl | H | 2 | α-naphthyl | CH | |
| 5.146 | Cl | H | 2 | α-naphthyl | CH | |
| 5.147 | Cl | H | 0 | —CH₂COOCH₃ | CH | |
| 5.148 | Cl | H | 2 | 4-fluorophenyl | CH | |
| 5.149 | Cl | H | 0 | 4-fluorophenyl | CH | |
| 5.150 | Cl | H | 0 | 4-nitrophenyl | CH | |
| 5.151 | Cl | H | 0 | 4-nitrophenyl | CH | |
| 5.152 | Cl | H | 2 | 2-nitrophenyl | CH | |
| 5.153 | Cl | H | 0 | 2-nitrophenyl | CH | |
| 5.154 | Cl | H | 2 | 2-trifluoromethyl | CH | |
| 5.155 | Cl | H | 0 | 2-trifluoromethyl | CH | |
| 5.156 | Cl | H | 2 | 4-methoxyphenyl | CH | |
| 5.157 | Cl | H | 0 | 4-methoxyphenyl | CH | |
| 5.158 | Cl | H | 2 | 2-methoxyphenyl | CH | |
| 5.159 | Cl | H | 0 | 2-methoxyphenyl | CH | |
| 5.160 | Cl | H | 2 | 2,4,6-trimethylphenyl | CH | |
| 5.161 | Cl | H | 0 | 2,4,6-trimethylphenyl | CH | |
| 5.162 | Cl | H | 0 | CS—N(CH₃)₂ | CH | |
| 5.163 | Cl | H | 0 | CSN(CH₂CH₃)₂ | CH | |
| 5.164 | Cl | H | 0 | CSN(CH₂CH₃)₂ | CH | |
| 5.165 | Cl | H | 0 | pyrrolidinothiocarbonyl | CH | 131–133° dec. |
| 5.166 | Cl | H | 0 | piperidinothiocarbonyl | CH | |
| 5.167 | Cl | H | 0 | N-phenylcarbamoylmethyl | CH | 110–112° |
| 5.168 | Cl | H | 0 | 2,4-dichlorophenyl | CH | |
| 5.169 | Cl | H | 2 | 2,4-dichlorophenyl | CH | |
| 5.170 | Cl | H | 0 | CH₂COOH | CH | 123–125° (dec.) |
| 5.171 | Cl | H | 0 | CH₂COO CH₃ | CH | |
| 5.172 | Cl | H | 0 | CH₂CON(CH₃)₂ | CH | |
| 5.173 | Cl | H | 0 | 4-chlorophenyl | N | |
| 5.174 | Cl | H | 0 | p-tolyl | N | |
| 5.175 | Cl | furyl-2- | 0 | 2-hydroxycarbonylphenyl | CH | |
| 5.176 | Cl | furyl-2- | 0 | 2-methoxycarbonylphenyl | CH | |
| 5.177 | Cl | furyl-2- | 0 | phenyl | CH | |
| 5.178 | Cl | 4-chlorophenyl | 0 | 2-hydroxycarbonylphenyl | CH | |
| 5.179 | Cl | 4-chlorophenyl | 0 | phenyl | CH | |
| 5.180 | Cl | CH₃ | 0 | 4-chlorophenyl | CH | |
| 5.181 | OCH₃ | H | 0 | phenyl | CH | |

TABLE 5-continued

[Structure: phenyl ring with R¹ substituent, connected to -SO₂NH-CON- group, with CH bearing R⁵ and S(O)ₘR⁹ substituents, connected to a triazine/pyrimidine ring with two CH₃ groups and E position]

| No | R¹ | R⁵ | m | R⁹ | E | m.p. (°C.) |
|---|---|---|---|---|---|---|
| 5.182 | OCH₃ | H | 2 | phenyl | CH | |
| 5.183 | OCH₃ | H | 0 | CSN(CH₃)₂ | CH | |
| 5.184 | OCH₃ | H | 0 | pyrrolidinothio-carbonyl | CH | |
| 5.185 | OCH₃ | H | 0 | CH₃ | CH | |
| 5.186 | OCH₃ | H | 2 | CH₃ | CH | |
| 5.187 | NO₂ | H | 0 | phenyl | CH | |
| 5.188 | NO₂ | H | 2 | phenyl | CH | |
| 5.189 | NO₂ | H | 0 | CSN(CH₃)₂ | CH | |
| 5.190 | NO₂ | H | 0 | pyrrolidinothio-carbonyl | CH | |
| 5.191 | NO₂ | H | 0 | CH₃ | CH | |
| 5.192 | NO₂ | H | 2 | CH₃ | CH | |
| 5.193 | CF₃ | H | 0 | phenyl | CH | |
| 5.194 | CF₃ | H | 2 | phenyl | CH | |
| 5.195 | CF₃ | H | 0 | CSN(CH₃)₂ | CH | |
| 5.196 | CF₃ | H | 0 | pyrrolidino-thiocarbonyl | CH | |
| 5.197 | CF₃ | H | 0 | CH₃ | CH | |
| 5.198 | CF₃ | H | 2 | CH₃ | CH | |
| 5.199 | OSO₂CH₃ | H | 0 | phenyl | CH | |
| 5.200 | OSO₂CH₃ | H | 2 | phenyl | CH | |
| 5.201 | OSO₂CH₃ | H | 0 | CSN(CH₃)₂ | CH | |
| 5.202 | OSO₂CH₃ | H | 0 | pyrrolidino-thiocarbonyl | CH | |
| 5.203 | OSO₂CH₃ | H | 0 | CH₃ | CH | |
| 5.204 | OSO₂CH₃ | H | 2 | CH₃ | CH | |
| 5.205 | OSO₂C₃H₇n | H | 2 | phenyl | CH | |
| 5.206 | OSO₂C₃H₇n | H | 2 | phenyl | CH | |
| 5.207 | OSO₂C₃H₇n | H | 0 | CSN(CH₃)₂ | CH | |
| 5.208 | OSO₂C₃H₇n | H | 0 | pyrrolidino-thiocarbonyl | CH | |
| 5.209 | OSO₂C₃H₇n | H | 2 | CH₃ | CH | |
| 5.210 | OSO₂C₃H₇n | H | 0 | CH₃ | CH | |
| 5.211 | SO₂N(CH₃)₂ | H | 0 | phenyl | CH | |
| 5.212 | SO₂N(CH₃)₂ | H | 2 | phenyl | CH | |
| 5.213 | SO₂N(CH₃)₂ | H | 0 | CSN(CH₃)₂ | CH | |
| 5.214 | SO₂N(CH₃)₂ | H | 0 | pyrrolidino-thiocarbonyl | CH | |
| 5.215 | SO₂N(CH₃)₂ | H | 0 | CH₃ | CH | |
| 5.216 | SO₂N(CH₃)₂ | H | 2 | CH₃ | CH | |
| 5.217 | CH₃ | H | 0 | phenyl | CH | |
| 5.218 | CH₃ | H | 2 | phenyl | CH | |
| 5.219 | CH₃ | H | 0 | CSN(CH₃)₂ | CH | |
| 5.220 | CH₃ | H | 0 | pyrrolidino-thiocarbonyl | CH | |
| 5.221 | CH₃ | H | 0 | CH₃ | CH | |
| 5.222 | CH₃ | H | 2 | CH₃ | CH | |
| 5.223 | SO₂CH₃ | H | 0 | phenyl | CH | |
| 5.224 | SO₂CH₃ | H | 2 | phenyl | CH | |
| 5.225 | SO₂CH₃ | H | 0 | CSN(CH₃)₂ | CH | |
| 5.226 | SO₂CH₃ | H | 0 | pyrrolidino-thiocarbonyl | CH | |
| 5.227 | SO₂CH₃ | H | 0 | CH₃ | CH | |
| 5.228 | SO₂CH₃ | H | 2 | CH₃ | CH | |
| 5.229 | CH₃ | H | 2 | p-tolyl | CH | 148–150° dec. |
| 5.230 | CH₃ | H | 0 | morpholino-thiocarbonyl | CH | 145–146° dec. |
| 5.231 | OCHF₂ | H | 0 | morpholino-thiocarbonyl | CH | 132–134° dec. |
| 5.232 | OCHF₂ | H | 0 | 4-fluorophenyl | CH | 125–127° |
| 5.233 | COOCH₃ | H | 0 | 4-fluorophenyl | CH | |
| 5.234 | COOCH₃ | H | 2 | 4-fluorophenyl | CH | |
| 5.235 | CH₃ | H | 2 | benzyl | CH | 146–148° dec. |
| 5.236 | CH₃ | H | 2 | 4-bromophenyl | CH | 141–143° dec. |
| 5.237 | Cl | CH₃ | 2 | p-tolyl | CH | 126–129° dec. |
| 5.238 | Cl | H | 0 | 2-carboxyphenyl | CH | 134–138° dec. |

TABLE 5-continued

| No | R¹ | R⁵ | m | R⁹ | E | m.p. (°C.) |
|---|---|---|---|---|---|---|
| 5.239 | 2,6-Cl₂ | H | 2 | benzyl | CH | 147–151° dec. |
| 5.240 | 2,6-Cl₂ | H | 0 | β-naphthyl | CH | 149–152° |
| 5.241 | 2,6-Cl₂ | H | 2 | p-tolyl | CH | 163–166 dec. |
| 5.242 | phenyl | H | 2 | CH₃ | CH | 162–166° dec. |
| 5.243 | phenyl | H | 2 | p-tolyl | CH | 154–157° dec. |
| 5.244 | phenyl | H | 0 | —CS—N(CH₃)₂ | CH | 143–145° dec. |
| 5.245 | phenyl | H | 0 | —CH₂—COOCH₃ | CH | 172–174° dec. |
| 5.246 | phenyl | H | 0 | —CH₂—CH₂—COOH | CH | 155–157 dec. |
| 5.247 | phenyl | H | 0 | —CH(CH₃)COOH | CH | 150–152° dec. |
| 5.248 | Cl | H | 2 | phenyl | N | |
| 5.249 | Cl | H | 2 | p-tolyl | N | |
| 5.250 | COOCH₃ | H | 2 | CH₃ | N | |
| 5.251 | OCHF₂ | H | 2 | p-tolyl | N | |
| 5.252 | NO₂ | H | 0 | C₂H₄COOH | CH | 121–124° |
| 5.253 | CF₃ | H | 0 | 4-chlorophenyl | CH | 118–121° |

TABLE 6

| No | R¹ | R⁵ | m | R⁹ | E | m.p. (°C.) |
|---|---|---|---|---|---|---|
| 6.001 | COOCH₃ | H | 2 | p-tolyl | CH | 148–150° (dec.) |
| 6.002 | COOCH₃ | H | 0 | p-tolyl | CH | |
| 6.003 | COOCH₃ | H | 2 | 4-chlorophenyl | CH | |
| 6.004 | COOCH₃ | H | 0 | 4-chlorophenyl | CH | |
| 6.005 | COOCH₃ | H | 0 | acetyl | CH | |
| 6.006 | COOCH₃ | H | 0 | benzoyl | CH | |
| 6.007 | COOCH₃ | H | 2 | CH₃ | CH | |
| 6.008 | COOCH₃ | H | 2 | CH₂CH₂CH₂CH₃ | CH | |
| 6.009 | COOCH₃ | H | 2 | CH(CH₃)₂ | CH | |
| 6.010 | COOCH₃ | H | 2 | benzyl | CH | 136–137° (dec.) |
| 6.011 | COOCH₃ | H | 2 | phenyl | CH | 141–142° (dec.) |
| 6.012 | COOCH₃ | H | 0 | phenyl | CH | |
| 6.013 | COOCH₃ | H | 2 | 4-bromophenyl | CH | 134–135° (dec.) |
| 6.014 | COOCH₃ | H | 0 | 4-bromophenyl | CH | |
| 6.015 | COOCH₃ | H | 2 | 2-chlorophenyl | CH | |
| 6.016 | COOCH₃ | H | 0 | 2-chlorophenyl | CH | |
| 6.017 | COOCH₃ | H | 0 | CH₃ | CH | |
| 6.018 | COOCH₃ | H | 0 | CH₂CH₂CH₂CH₃ | CH | |
| 6.019 | COOCH₃ | H | 0 | CH(CH₃)₂ | CH | |
| 6.020 | COOCH₃ | H | 0 | benzyl | CH | |
| 6.021 | COOCH₃ | H | 2 | β-naphthyl | CH | 140–141° (dec.) |
| 6.022 | COOCH₃ | H | 0 | β-naphthyl | CH | |
| 6.023 | COOCH₃ | H | 2 | 1,2,4-trichlorophenyl | CH | |
| 6.024 | COOCH₃ | H | 0 | 1,2,4-trichlorophenyl | CH | |
| 6.025 | COOCH₃ | H | 2 | α-naphthyl | CH | |
| 6.026 | COOCH₃ | H | 2 | α-naphthyl | CH | |
| 6.027 | COOCH₃ | H | 0 | —CH₂COOCH₃ | CH | |
| 6.028 | COOCH₃ | H | 2 | 4-fluorophenyl | CH | |
| 6.029 | COOCH₃ | H | 0 | 4-fluorophenyl | CH | |
| 6.030 | COOCH₃ | H | 0 | 4-nitrophenyl | CH | |
| 6.031 | COOCH₃ | H | 0 | 4-nitrophenyl | CH | |
| 6.032 | COOCH₃ | H | 2 | 2-nitrophenyl | CH | |

TABLE 6-continued

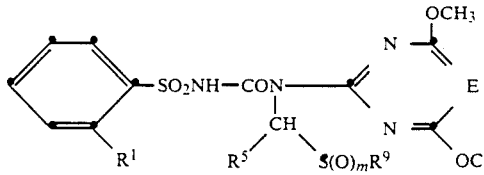

| No. | $R^1$ | $R^5$ | m | $S(O)_mR^9$ | E | mp |
|---|---|---|---|---|---|---|
| 6.033 | COOCH$_3$ | H | 0 | 2-nitrophenyl | CH | |
| 6.034 | COOCH$_3$ | H | 2 | 2-trifluoromethyl-phenyl | CH | |
| 6.035 | COOCH$_3$ | H | 0 | 2-trifluoromethyl-phenyl | CH | |
| 6.036 | COOCH$_3$ | H | 2 | 4-methoxyphenyl | CH | |
| 6.037 | COOCH$_3$ | H | 0 | 4-methoxyphenyl | CH | |
| 6.038 | COOCH$_3$ | H | 2 | 2-methoxyphenyl | CH | |
| 6.039 | COOCH$_3$ | H | 0 | 2-methoxyphenyl | CH | |
| 6.040 | COOCH$_3$ | H | 2 | 2,4,6-trimethyl-phenyl | CH | 133–134° (dec.) |
| 6.041 | COOCH$_3$ | H | 0 | 2,4,6-trimethyl-phenyl | CH | |
| 6.042 | COOCH$_3$ | H | 0 | CS—N(CH$_3$)$_2$ | CH | |
| 6.043 | COOCH$_3$ | H | 0 | CSN(CH$_2$CH$_3$)$_2$ | CH | 139–140° (dec.) |
| 6.044 | COOCH$_3$ | H | 0 | CSN(CH$_2$CH$_3$)$_2$ | N | |
| 6.045 | COOCH$_3$ | H | 0 | pyrrolidinothio-carbonyl | CH | |
| 6.046 | COOCH$_3$ | H | 0 | piperidinothio-carbonyl | CH | |
| 6.047 | COOCH$_3$ | H | 0 | N-phenylcarbamoyl-methyl | CH | |
| 6.048 | COOCH$_3$ | H | 0 | 2,4-dichlorophenyl | CH | |
| 6.049 | COOCH$_3$ | H | 2 | 2,4-dichlorophenyl | CH | |
| 6.050 | COOCH$_3$ | H | 0 | CH$_2$COOH | CH | |
| 6.051 | COOCH$_3$ | H | 0 | CH$_2$COOCH$_3$ | CH | |
| 6.052 | COOCH$_3$ | H | 0 | CH$_2$CON(CH$_3$)$_2$ | CH | |
| 6.053 | COOCH$_3$ | H | 0 | 4-Chlorophenyl | N | |
| 6.054 | COOCH$_3$ | H | 0 | p-tolyl | N | |
| 6.055 | COOCH$_3$ | furyl-2- | 0 | 2-hydroxy-carbonylphenyl | CH | |
| 6.056 | COOCH$_3$ | furyl-2- | 0 | 2-methoxy-carbonylphenyl | CH | |
| 6.057 | COOCH$_3$ | furyl-2- | 0 | phenyl | CH | |
| 6.058 | COOCH$_3$ | 4-chloro-phenyl | 0 | 2-hydroxy-carbonylphenyl | CH | |
| 6.059 | COOCH$_3$ | 4-chloro-phenyl | 0 | phenyl | CH | |
| 6.060 | COOCH$_3$ | CH$_3$ | 0 | 4-chlorophenyl | CH | |
| 6.061 | OCHF$_2$ | H | 2 | p-tolyl | CH | 142–143° |
| 6.062 | OCHF$_2$ | H | 0 | p-tolyl | CH | |
| 6.063 | OCHF$_2$ | H | 2 | 4-chlorophenyl | CH | |
| 6.064 | OCHF$_2$ | H | 0 | 4-chlorophenyl | CH | |
| 6.065 | OCHF$_2$ | H | 0 | acetyl | CH | |
| 6.066 | OCHF$_2$ | H | 0 | benzoyl | CH | |
| 6.067 | OCHF$_2$ | H | 2 | CH$_3$CH | | |
| 6.068 | OCHF$_2$ | H | 2 | CH$_2$CH$_2$CH$_2$CH$_3$ | CH | |
| 6.069 | OCHF$_2$ | H | 2 | CH(CH$_3$)$_2$ | CH | |
| 6.070 | OCHF$_2$ | H | 2 | benzyl | CH | |
| 6.071 | OCHF$_2$ | H | 2 | phenyl | CH | |
| 6.072 | OCHF$_2$ | H | 0 | phenyl | CH | |
| 6.073 | OCHF$_2$ | H | 2 | 4-bromophenyl | CH | |
| 6.074 | OCHF$_2$ | H | 0 | 4-bromophenyl | CH | |
| 6.075 | OCHF$_2$ | H | 2 | 2-chlorophenyl | CH | |
| 6.076 | OCHF$_2$ | H | 0 | 2-chlorophenyl | CH | |
| 6.077 | OCHF$_2$ | H | 0 | CH$_3$CH | | |
| 6.078 | OCHF$_2$ | H | 0 | CH$_2$CH$_2$CH$_2$CH$_3$ | CH | |
| 6.079 | OCHF$_2$ | H | 0 | CH(CH$_3$)$_2$ | CH | |
| 6.080 | OCHF$_2$ | H | 0 | benzyl | CH | |
| 6.081 | OCHF$_2$ | H | 2 | β-naphthyl | CH | |
| 6.082 | OCHF$_2$ | H | 0 | β-naphthyl | CH | |
| 6.083 | OCHF$_2$ | H | 2 | 1,2,4-trichloro-phenyl | CH | |
| 6.084 | OCHF$_2$ | H | 0 | 1,2,4-trichloro-phenyl | CH | |
| 6.085 | OCHF$_2$ | H | 2 | α-naphthyl | CH | |
| 6.086 | OCHF$_2$ | H | 2 | α-naphthyl | CH | |
| 6.087 | OCHF$_2$ | H | 0 | —CH$_2$COOCH$_3$ | CH | |
| 6.088 | OCHF$_2$ | H | 2 | 4-fluorophenyl | CH | |
| 6.089 | OCHF$_2$ | H | 0 | 4-fluorophenyl | CH | |
| 6.090 | OCHF$_2$ | H | 0 | 4-nitrophenyl | CH | |
| 6.091 | OCHF$_2$ | H | 0 | 4-nitrophenyl | CH | |
| 6.092 | OCHF$_2$ | H | 2 | 2-nitrophenyl | CH | |
| 6.093 | OCHF$_2$ | H | 0 | 2-nitrophenyl | CH | |

TABLE 6-continued

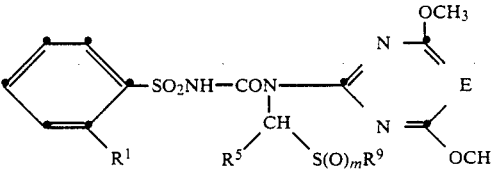

| | R¹ | R⁵ | | S(O)$_m$R⁹ | E |
|---|---|---|---|---|---|
| 6.094 | OCHF$_2$ | H | 2 | 2-trifluoromethyl | CH |
| 6.095 | OCHF$_2$ | H | 0 | 2-trifluoromethyl | CH |
| 6.096 | OCHF$_2$ | H | 2 | 4-methoxyphenyl | CH |
| 6.097 | OCHF$_2$ | H | 0 | 4-methoxyphenyl | CH |
| 6.098 | OCHF$_2$ | H | 2 | 2-methoxyphenyl | CH |
| 6.099 | OCHF$_2$ | H | 0 | 2-methoxyphenyl | CH |
| 6.100 | OCHF$_2$ | H | 2 | 2,4,6-trimethyl-phenyl | CH |
| 6.101 | OCHF$_2$ | H | 0 | 2,4,6-trimethyl-phenyl | CH |
| 6.102 | OCHF$_2$ | H | 0 | CS—N(CH$_3$)$_2$ | CH |
| 6.103 | OCHF$_2$ | H | 0 | CSN(CH$_2$CH$_3$)$_2$ | CH |
| 6.104 | OCHF$_2$ | H | 0 | CSN(CH$_2$CH$_3$)$_2$ | CH |
| 6.105 | OCHF$_2$ | H | 0 | pyrrolidinothio-carbonyl | CH |
| 6.106 | OCHF$_2$ | H | 0 | piperidinothio-carbonyl | CH |
| 6.107 | OCHF$_2$ | H | 0 | N-phenylcarbamoyl-methyl | CH |
| 6.108 | OCHF$_2$ | H | 0 | 2,4-dichlorophenyl | CH |
| 6.109 | OCHF$_2$ | H | 2 | 2,4-dichlorophenyl | CH |
| 6.110 | OCHF$_2$ | H | 0 | CH$_2$COOH | CH |
| 6.111 | OCHF$_2$ | H | 0 | CH$_2$COOCH$_3$ | CH |
| 6.112 | OCHF$_2$ | H | 0 | CH$_2$CON(CH$_3$)$_2$ | CH |
| 6.113 | OCHF$_2$ | H | 0 | 4-chlorophenyl | N |
| 6.114 | OCHF$_2$ | H | 0 | p-tolyl | N |
| 6.115 | OCHF$_2$ | furyl-2- | 0 | 2-hydroxy-carbonylphenyl | CH |
| 6.116 | OCHF$_2$ | furyl-2- | 0 | 2-methoxy-carbonylphenyl | CH |
| 6.117 | OCHF$_2$ | furyl-2- | 0 | phenyl | CH |
| 6.118 | OCHF$_2$ | 4-chloro-phenyl | 0 | 2-hydroxy-carbonylphenyl | CH |
| 6.119 | OCHF$_2$ | 4-chloro-phenyl | 0 | phenyl | CH |
| 6.120 | OCHF$_2$ | CH$_3$ | 0 | 4-chlorophenyl | CH |
| 6.121 | Cl | H | 2 | p-tolyl | CH |
| 6.122 | Cl | H | 0 | p-tolyl | CH |
| 6.123 | Cl | H | 2 | 4-chlorophenyl | CH |
| 6.124 | Cl | H | 0 | 4-chlorophenyl | CH |
| 6.125 | Cl | H | 0 | acetyl | CH |
| 6.126 | Cl | H | 0 | benzoyl | CH |
| 6.127 | Cl | H | 2 | CH$_3$ | CH |
| 6.128 | Cl | H | 2 | CH$_2$CH$_2$CH$_2$CH$_3$ | CH |
| 6.129 | Cl | H | 2 | CH(CH$_3$)$_2$ | CH |
| 6.130 | Cl | H | 2 | benzyl | CH |
| 6.131 | Cl | H | 2 | phenyl | CH |
| 6.132 | Cl | H | 0 | phenyl | CH |
| 6.133 | Cl | H | 2 | 4-bromophenyl | CH |
| 6.134 | Cl | H | 0 | 4-bromophenyl | CH |
| 6.135 | Cl | H | 2 | 2-chlorophenyl | CH |
| 6.136 | Cl | H | 0 | 2-chlorophenyl | CH |
| 6.137 | Cl | H | 0 | CH$_3$CH | CH |
| 6.138 | Cl | H | 0 | CH$_2$CH$_2$CH$_2$CH$_3$ | CH |
| 6.139 | Cl | H | 0 | CH(CH$_3$)$_2$ | CH |
| 6.140 | Cl | H | 0 | benzyl | CH |
| 6.141 | Cl | H | 2 | β-naphthyl | CH |
| 6.142 | Cl | H | 0 | β-naphthyl | CH |
| 6.143 | Cl | H | 2 | 1,2,4-trichloro-phenyl | CH |
| 6.144 | Cl | H | 0 | 1,2,4-trichloro-phenyl | CH |
| 6.145 | Cl | H | 2 | α-naphthyl | CH |
| 6.146 | Cl | H | 2 | α-naphthyl | CH |
| 6.147 | Cl | H | 0 | —CH$_2$COOCH$_3$ | CH |
| 6.148 | Cl | H | 2 | 4-fluorophenyl | CH |
| 6.149 | Cl | H | 0 | 4-fluorophenyl | CH |
| 6.150 | Cl | H | 0 | 4-nitrophenyl | CH |
| 6.151 | Cl | H | 0 | 4-nitrophenyl | CH |
| 6.152 | Cl | H | 2 | 2-nitrophenyl | CH |
| 6.153 | Cl | H | 0 | 2-nitrophenyl | CH |
| 6.154 | Cl | H | 2 | 2-trifluoromethyl | CH |
| 6.155 | Cl | H | 0 | 2-trifluoromethyl | CH |
| 6.156 | Cl | H | 2 | 4-methoxyphenyl | CH |

TABLE 6-continued

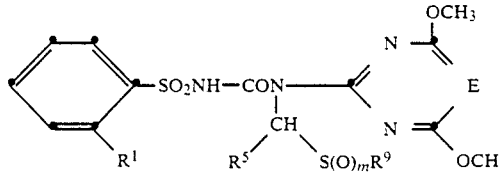

| | $R^1$ | $R^5$ | m | $S(O)_mR^9$ | E |
|---|---|---|---|---|---|
| 6.157 | Cl | H | 0 | 4-methoxyphenyl | CH |
| 6.158 | Cl | H | 2 | 2-methoxyphenyl | CH |
| 6.159 | Cl | H | 0 | 2-methoxyphenyl | CH |
| 6.160 | Cl | H | 2 | 2,4,6-trimethylphenyl | CH |
| 6.161 | Cl | H | 0 | 2,4,6-trimethylphenyl | CH |
| 6.162 | Cl | H | 0 | CS—N(CH$_3$)$_2$ | CH |
| 6.163 | Cl | H | 0 | CSN(CH$_2$CH$_3$)$_2$ | CH |
| 6.164 | Cl | H | 0 | CSN(CH$_2$CH$_3$)$_2$ | CH |
| 6.165 | Cl | H | 0 | pyrrolidinothiocarbonyl | CH |
| 6.166 | Cl | H | 0 | piperidinothiocarbonyl | CH |
| 6.167 | Cl | H | 0 | N-phenylcarbamoylmethyl | CH |
| 6.168 | Cl | H | 0 | 2,4-dichlorophenyl | CH |
| 6.169 | Cl | H | 2 | 2,4-dichlorophenyl | CH |
| 6.170 | Cl | H | 0 | CH$_2$COOH | CH |
| 6.171 | Cl | H | 0 | CH$_2$COOCH$_3$ | CH |
| 6.172 | Cl | H | 0 | CH$_2$CON(CH$_3$)$_2$ | CH |
| 6.173 | Cl | H | 0 | 4-chlorophenyl | N |
| 6.174 | Cl | H | 0 | p-tolyl | N |
| 6.175 | Cl | furyl-2- | 0 | 2-hydroxycarbonylphenyl | CH |
| 6.176 | Cl | furyl-2- | 0 | 2-methoxycarbonylphenyl | CH |
| 6.177 | Cl | furyl-2- | 0 | phenyl | CH |
| 6.178 | Cl | 4-chlorophenyl | 0 | 2-hydroxycarbonylphenyl | CH |
| 6.179 | Cl | 4-chlorophenyl | 0 | phenyl | CH |
| 6.180 | Cl | CH$_3$ | 0 | 4-chlorophenyl | CH |
| 6.181 | OCH$_3$ | H | 0 | phenyl | CH |
| 6.182 | OCH$_3$ | H | 2 | phenyl | CH |
| 6.183 | OCH$_3$ | H | 0 | CSN(CH$_3$)$_2$ | CH |
| 6.184 | OCH$_3$ | H | 0 | pyrrolidinothiocarbonyl | CH |
| 6.185 | OCH$_3$ | H | 0 | CH$_3$ | CH |
| 6.186 | OCH$_3$ | H | 2 | CH$_3$ | CH |
| 6.187 | NO$_2$ | H | 0 | phenyl | CH |
| 6.188 | NO$_2$ | H | 2 | phenyl | CH |
| 6.189 | NO$_2$ | H | 0 | CSN(CH$_3$)$_2$ | CH |
| 6.190 | NO$_2$ | H | 0 | pyrrolidinothiocarbonyl | CH |
| 6.191 | NO$_2$ | H | 0 | CH$_3$ | CH |
| 6.192 | NO$_2$ | H | 2 | CH$_3$ | CH |
| 6.193 | CF$_3$ | H | 0 | phenyl | CH |
| 6.194 | CF$_3$ | H | 2 | phenyl | CH |
| 6.195 | CF$_3$ | H | 0 | CSN(CH$_3$)$_2$ | CH |
| 6.196 | CF$_3$ | H | 0 | pyrrolidinothiocarbonyl | CH |
| 6.197 | CF$_3$ | H | 0 | CH$_3$ | CH |
| 6.198 | CF$_3$ | H | 2 | CH$_3$ | CH |
| 6.199 | OSO$_2$CH$_3$ | H | 0 | phenyl | CH |
| 6.200 | OSO$_2$CH$_3$ | H | 2 | phenyl | CH |
| 6.201 | OSO$_2$CH$_3$ | H | 0 | CSN(CH$_3$)$_2$ | CH |
| 6.202 | OSO$_2$CH$_3$ | H | 0 | pyrrolidinothiocarbonyl | CH |
| 6.203 | OSO$_2$CH$_3$ | H | 0 | CH$_3$ | CH |
| 6.204 | OSO$_2$CH$_3$ | H | 2 | CH$_3$ | CH |
| 6.205 | OSO$_2$C$_3$H$_7$n | H | 2 | phenyl | CH |
| 6.206 | OSO$_2$C$_3$H$_7$n | H | 2 | phenyl | CH |
| 6.207 | OSO$_2$C$_3$H$_7$n | H | 0 | CSN(CH$_3$)$_2$ | CH |
| 6.208 | OSO$_2$C$_3$H$_7$n | H | 0 | pyrrolidinothiocarbonyl | CH |
| 6.209 | OSO$_2$C$_3$H$_7$n | H | 2 | CH$_3$ | CH |
| 6.210 | OSO$_2$C$_3$H$_7$n | H | 0 | CH$_3$ | CH |
| 6.211 | SO$_2$N(CH$_3$)$_2$ | H | 0 | phenyl | CH |
| 6.212 | SO$_2$N(CH$_3$)$_2$ | H | 2 | phenyl | CH |
| 6.213 | SO$_2$N(CH$_3$)$_2$ | H | 0 | CSN(CH$_3$)$_2$ | CH |
| 6.214 | SO$_2$N(CH$_3$)$_2$ | H | 0 | pyrrolidinothiocarbonyl | CH |
| 6.215 | SO$_2$N(CH$_3$)$_2$ | H | 0 | CH$_3$ | CH |

TABLE 6-continued

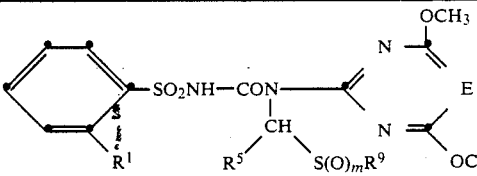

| No. | R¹ (R²) | R⁵ | m | R⁹ | E | m.p. (°C.) |
|---|---|---|---|---|---|---|
| 6.216 | SO₂N(CH₃)₂ | H | 2 | CH₃ | CH | |
| 6.217 | CH₃ | H | 0 | phenyl | CH | |
| 6.218 | CH₃ | H | 2 | phenyl | CH | |
| 6.219 | CH₃ | H | 0 | CSN(CH₃)₂ | CH | |
| 6.220 | CH₃ | H | 0 | pyrrolidino-thiocarbonyl | CH | |
| 6.221 | CH₃ | H | 0 | CH₃ | CH | |
| 6.222 | CH₃ | H | 2 | CH₃ | CH | |
| 6.223 | SO₂CH₃ | H | 0 | phenyl | CH | |
| 6.224 | SO₂CH₃ | H | 2 | phenyl | CH | |
| 6.225 | SO₂CH₃ | H | 0 | CSN(CH₃)₂ | CH | |
| 6.226 | SO₂CH₃ | H | 0 | pyrrolidino-thiocarbonyl | CH | |
| 6.227 | SO₂CH₃ | H | 0 | CH₃ | CH | |
| 6.228 | SO₂CH₃ | H | 2 | CH₃ | CH | |
| 6.229 | phenyl | H | 0 | p-tolyl | CH | 144–147° |
| 6.230 | phenyl | H | 2 | p-tolyl | CH | 141–144° dec. |
| 6.231 | COOCH₃ | H | 2 | benzyl | N | |
| 6.232 | COOCH₃ | H | 2 | phenyl | N | |
| 6.233 | OCF₂CHF₂ | H | 2 | p-tolyl | CH | 133–134° |
| 6.234 | OCF₂CHF₂ | H | 2 | p-tolyl | CH | |
| 6.235 | OCF₂CHF₂ | H | 2 | CH₃ | CH | |
| 6.236 | OCF₂CHF₂ | H | 2 | phenyl | CH | |
| 6.237 | OCF₂CHF₂ | H | 2 | 4-chlorophenyl | CH | |
| 6.238 | OCF₂CHF₂ | H | 2 | β-naphthyl | CH | |
| 6.239 | F | H | 0 | 4-chlorophenyl | CH | |
| 6.240 | F | H | 0 | β-naphthyl | CH | 158–154° |
| 6.241 | F | H | 2 | β-naphthyl | CH | |
| 6.242 | COOCH₃ | H | 2 | 2-methoxy-carbonylbenzyl | CH | 66–67° |
| 6.243 | COOCH₃ | H | 2 | C₃H₇n | CH | |
| 6.244 | COOCH₃ | H | 2 | C₂H₅ | CH | |
| 6.245 | COOCH₃ | H | 2 | 2-difluoromethoxy-phenyl | CH | 145–147° |
| 6.246 | COOCH₃ | H | 2 | 3,4-dichlorophenyl | CH | |
| 6.247 | COOCH₃ | H | 2 | 3,5-dichlorophenyl | CH | |
| 6.248 | COOCH₃ | H | 2 | 3-chlorophenyl | CH | |
| 6.249 | COOCH₃ | H | 2 | 2-difluoromethyl-thiophenyl | CH | |
| 6.250 | COOCH₃ | H | 2 | 3-trifluoromethyl-phenyl | CH | |
| 6.251 | COOCH₃ | H | 2 | 2,5-dimethyl-phenyl | CH | |
| 6.252 | COOC₂H₅ | H | 2 | CH₃ | CH | |
| 6.253 | COOC₂H₅ | H | 2 | C₃H₇n | CH | |
| 6.254 | COOC₂H₅ | H | 2 | phenyl | CH | 149° |
| 6.255 | COOC₂H₅ | H | 2 | p-tolyl | CH | 147° |
| 6.256 | COOC₂H₅ | H | 0 | CSN(CH₃)₂ | CH | |
| 6.257 | NO₂ | H | 2 | p-tolyl | CH | 149–151° (dec.) |
| 6.258 | NO₂ | H | 2 | 4-chlorophenyl | CH | 164° (dec.) |
| No. | R¹ (R²) | R⁵ | m | R⁹ | E | m.p. (°C.) |
| 6.259 | NO₂ | H | 2 | 4-bromophenyl | CH | |
| 6.260 | NO₂ | H | 2 | β-naphthyl | CH | |
| 6.261 | NO₂ | H | 2 | C₂H₅ | CH | |
| 6.262 | NO₂ | H | 2 | C₃H₇n | CH | |
| 6.263 | NO₂ | H | 2 | benzyl | CH | |
| 6.264 | NO₂ | H | 2 | 2-methoxy-carbonylbenzyl | CH | |
| 6.265 | NO₂ | H | 2 | 4-methoxy-phenyl | CH | |
| 6.266 | NO₂ | H | 2 | 2-difluoro-methoxyphenyl | CH | |
| 6.267 | NO₂ | H | 2 | mesityl | CH | |
| 6.268 | OCF₃ | H | 2 | p-tolyl | CH | 138–139° (dec.) |
| 6.269 | OC₂H₄OCH₃ | H | 2 | p-tolyl | CH | 135–137° (dec.) |
| 6.270 | OC₂H₄Cl | H | 2 | p-tolyl | CH | 133–135° (dec.) |
| 6.271 | OCCl=CHCl | | 2 | p-tolyl | CH | 143–144° (dec.) |
| 6.272 | CF₃ | | 2 | p-tolyl | CH | 156–158° (dec.) |
| 6.273 | OSO₂CH₃ | | 2 | p-tolyl | CH | |
| 6.274 | OSO₂N(CH₃)₂ | | 2 | p-tolyl | CH | |
| 6.275 | OCH₃ | | 2 | p-tolyl | CH | 164° (dec.) |
| 6.276 | OCH₃ | | 2 | 4-bromophenyl | CH | 165° (dec.) |
| 6.277 | OCH₃ | | 2 | β-naphthyl | CH | 148–150° (dec.) |

TABLE 6-continued

[Structure: phenyl-SO₂NH-CON(CH(R⁵)S(O)ₘR⁹)-C(=N-)(...)... with OCH₃, E, OCH₃ substituents on triazine]

| No | R¹ | m | R⁹ | E | m.p.(°C.) |
|---|---|---|---|---|---|
| 6.278 | OCH₃ | 2 | benzyl | CH | 126–128° (dec.) |
| 6.279 | CF₃ | 2 | p-tolyl | CH | 156–158° (dec.) |
| 6.280 | CF₃ | 2 | 4-chlorophenyl | CH | 147–154° (dec.) |
| 6.281 | CF₃ | 2 | β-naphthyl | CH | 152–154° (dec.) |

TABLE 7

[Structure: phenyl(R¹)-SO₂-NH-CO-N(CH(R⁵)S(O)ₘR⁹)-pyrimidine with OCH₃, E, CH₃ substituents]

| No | R¹ | R⁵ | m | R⁹ | E | m.p.(°C.) |
|---|---|---|---|---|---|---|
| 7.001 | COOCH₃ | H | 2 | p-tolyl | CH | 153–158° dec. |
| 7.002 | COOCH₃ | H | 0 | p-tolyl | CH | |
| 7.003 | COOCH₃ | H | 2 | 4-chlorophenyl | CH | |
| 7.004 | COOCH₃ | H | 0 | 4-chlorophenyl | CH | |
| 7.005 | COOCH₃ | H | 0 | acetyl | CH | |
| 7.006 | COOCH₃ | H | 0 | benzoyl | CH | |
| 7.007 | COOCH₃ | H | 2 | CH₃ | CH | |
| 7.008 | COOCH₃ | H | 2 | CH₂CH₂CH₂CH₃ | CH | |
| 7.009 | COOCH₃ | H | 2 | CH(CH₃)₂ | CH | |
| 7.010 | COOCH₃ | H | 2 | benzyl | CH | |
| 7.011 | COOCH₃ | H | 2 | phenyl | CH | |
| 7.012 | COOCH₃ | H | 0 | phenyl | CH | |
| 7.013 | COOCH₃ | H | 2 | 4-bromophenyl | CH | |
| 7.014 | COOCH₃ | H | 0 | 4-bromophenyl | CH | |
| 7.015 | COOCH₃ | H | 2 | 2-chlorophenyl | CH | |
| 7.016 | COOCH₃ | H | 0 | 2-chlorophenyl | CH | |
| 7.017 | COOCH₃ | H | 0 | CH₃ | CH | |
| 7.018 | COOCH₃ | H | 0 | CH₂CH₂CH₂CH₃ | CH | |
| 7.019 | COOCH₃ | H | 0 | CH(CH₃)₂ | CH | |
| 7.020 | COOCH₃ | H | 0 | benzyl | CH | |
| 7.021 | COOCH₃ | H | 2 | β-naphthyl | CH | |
| 7.022 | COOCH₃ | H | 0 | β-naphthyl | CH | |
| 7.023 | COOCH₃ | H | 2 | 1,2,4-trichlorophenyl | CH | |
| 7.024 | COOCH₃ | H | 0 | 1,2,4-trichlorophenyl | CH | |
| 7.025 | COOCH₃ | H | 2 | α-naphthyl | CH | |
| 7.026 | COOCH₃ | H | 2 | α-naphthyl | CH | |
| 7.027 | COOCH₃ | H | 0 | —CH₂COOCH₃ | CH | |
| 7.028 | COOCH₃ | H | 2 | 4-fluorophenyl | CH | |
| 7.029 | COOCH₃ | H | 0 | 4-fluorophenyl | CH | |
| 7.030 | COOCH₃ | H | 0 | 4-nitrophenyl | CH | |
| 7.031 | COOCH₃ | H | 0 | 4-nitrophenyl | CH | |
| 7.032 | COOCH₃ | H | 2 | 2-nitorphenyl | CH | |
| 7.033 | COOCH₃ | H | 0 | 2-nitrophenyl | CH | |
| 7.034 | COOCH₃ | H | 2 | 2-trifluoromethyl | CH | |
| 7.035 | COOCH₃ | H | 0 | 2-trifluoromethyl | CH | |
| 7.036 | COOCH₃ | H | 2 | 4-methoxyphenyl | CH | |
| 7.037 | COOCH₃ | H | 0 | 4-methoxyphenyl | CH | |
| 7.038 | COOCH₃ | H | 2 | 2-methoxyphenyl | CH | |
| 7.039 | COOCH₃ | H | 0 | 2-methoxyphenyl | CH | |
| 7.040 | COOCH₃ | H | 2 | 2,4,6-trimethylphenyl | CH | |
| 7.041 | COOCH₃ | H | 0 | 2,4,6-trimethylphenyl | CH | |
| 7.042 | COOCH₃ | H | 0 | CS—N(CH₃)₂ | CH | |
| 7.043 | COOCH₃ | H | 0 | CSN(CH₃CH₃)₂ | CH | |
| 7.044 | COOCH₃ | H | 0 | CSN(CH₂CH₃)₂ | CH | |
| 7.045 | COOCH₃ | H | 0 | pyrrolidinothiocarbonyl | CH | |
| 7.046 | COOCH₃ | H | 0 | piperidinothiocarbonyl | CH | |
| 7.047 | COOCH₃ | H | 0 | N-phenylcarbamoylmethyl | CH | |

TABLE 7-continued

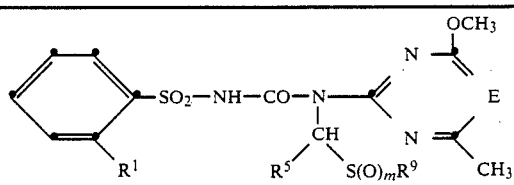

| No | R¹ | R⁵ | m | R⁹ | E | m.p.(°C.) |
|---|---|---|---|---|---|---|
| 7.048 | COOCH₃ | H | 0 | 2,4-dichlorophenyl | CH | |
| 7.049 | COOCH₃ | H | 2 | 2,4-dichlorophenyl | CH | |
| 7.050 | COOCH₃ | H | 0 | CH₂COOH | CH | |
| 7.051 | COOCH₃ | H | 0 | CH₂COOCH₃ | CH | |
| 7.052 | COOCH₃ | H | 0 | CH₂CON(CH₃)₂ | CH | |
| 7.053 | COOCH₃ | H | 0 | 4-chlorophenyl | N | |
| 7.054 | COOCH₃ | H | 0 | p-tolyl | N | |
| 7.055 | COOCH₃ | furyl-2- | 0 | 2-hydroxy-carbonylphenyl | CH | |
| 7.056 | COOCH₃ | furyl-2- | 0 | 2-methoxy-carbonylphenyl | CH | |
| 7.057 | COOCH₃ | furyl-2- | 0 | phenyl | CH | |
| 7.058 | COOCH₃ | 4-chloro-phenyl | 0 | 2-hydroxy-carbonylphenyl | CH | |
| 7.059 | COOCH₃ | 4-chloro-phenyl | 0 | phenyl | CH | |
| 7.060 | COOCH₃ | CH₃ | 0 | 4-chlorophenyl | CH | |
| 7.061 | OCHF₂ | H | 2 | p-tolyl | CH | 146–150° |
| 7.062 | OCHF₂ | H | 0 | p-tolyl | CH | |
| 7.063 | OCHF₂ | H | 2 | 4-chlorophenyl | CH | |
| 7.064 | OCHF₂ | H | 0 | 4-chlorophenyl | CH | |
| 7.065 | OCHF₂ | H | 0 | acetyl | CH | |
| 7.066 | OCHF₂ | H | 0 | benzoyl | CH | |
| 7.067 | OCHF₂ | H | 2 | CH₃ | N | |
| 7.068 | OCHF₂ | H | 2 | CH₂CH₂CH₂CH₃ | CH | |
| 7.069 | OCHF₂ | H | 2 | CH(CH₃)₂ | CH | |
| 7.070 | OCHF₂ | H | 2 | benzyl | CH | |
| 7.071 | OCHF₂ | H | 2 | phenyl | CH | |
| 7.072 | OCHF₂ | H | 0 | phenyl | CH | |
| 7.073 | OCHF₂ | H | 2 | 4-bromophenyl | CH | |
| 7.074 | OCHF₂ | H | 0 | 4-bromophenyl | CH | |
| 7.075 | OCHF₂ | H | 2 | 2-chlorophenyl | CH | |
| 7.076 | OCHF₂ | H | 0 | 2-chlorophenyl | CH | |
| 7.077 | OCHF₂ | H | 0 | CH₃ | N | |
| 7.078 | OCHF₂ | H | 0 | CH₂CH₂CH₂CH₃ | CH | |
| 7.079 | OCHF₂ | H | 0 | CH(CH₃)₂ | CH | |
| 7.080 | OCHF₂ | H | 0 | benzyl | CH | |
| 7.081 | OCHF₂ | H | 2 | β-naphthyl | CH | |
| 7.082 | OCHF₂ | H | 0 | β-naphthyl | CH | 162–164° |
| 7.083 | OCHF₂ | H | 2 | 1,2,4-trichloro-phenyl | CH | |
| 7.084 | OCHF₂ | H | 0 | 2,4,5-trichloro-phenyl | CH | 104–107° |
| 7.085 | OCHF₂ | H | 2 | α-naphthyl | CH | |
| 7.086 | OCHF₂ | H | 2 | α-naphthyl | CH | |
| 7.087 | OCHF₂ | H | 0 | —CH₂COOCH₃ | CH | |
| 7.088 | OCHF₂ | H | 2 | 4-fluorophenyl | CH | |
| 7.089 | OCHF₂ | H | 0 | 4-fluorophenyl | CH | |
| 7.090 | OCHF₂ | H | 0 | 4-nitrophenyl | CH | |
| 7.091 | OCHF₂ | H | 0 | 4-nitrophenyl | CH | |
| 7.092 | OCHF₂ | H | 2 | 2-nitrophenyl | CH | |
| 7.093 | OCHF₂ | H | 0 | 2-nitrophenyl | CH | |
| 7.094 | OCHF₂ | H | 2 | 2-trifluoromethyl | CH | |
| 7.095 | OCHF₂ | H | 0 | 2-trifluoromethyl | CH | |
| 7.096 | OCHF₂ | H | 2 | 4-methoxyphenyl | CH | |
| 7.097 | OCHF₂ | H | 0 | 4-methoxyphenyl | CH | |
| 7.098 | OCHF₂ | H | 2 | 2-methoxyphenyl | CH | |
| 7.099 | OCHF₂ | H | 0 | 2-methoxyphenyl | CH | |
| 7.100 | OCHF₂ | H | 2 | 2,4,6-trimethyl-phenyl | CH | |
| 7.101 | OCHF₂ | H | 0 | 2,4,6-trimethyl-phenyl | CH | |
| 7.102 | OCHF₂ | H | 0 | CS—N(CH₃)₂ | CH | |
| 7.103 | OCHF₂ | H | 0 | CSN(CH₂CH₃)₂ | CH | |
| 7.104 | OCHF₂ | H | 0 | CSN(CH₂CH₃)₂ | CH | |
| 7.105 | OCHF₂ | H | 0 | pyrrolidinothio-carbonyl | CH | |
| 7.106 | OCHF₂ | H | 0 | piperidinothio-carbonyl | CH | |
| 7.107 | OCHF₂ | H | 0 | N-phenylcarbamoyl-methyl | CH | |
| 7.108 | OCHF₂ | H | 0 | 2,4-dichlorophenyl | CH | |

TABLE 7-continued

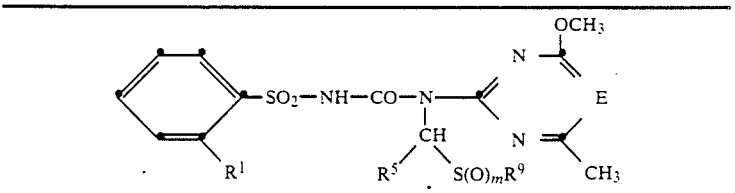

| No | R¹ | R⁵ | m | R⁹ | E | m.p.(°C.) |
|---|---|---|---|---|---|---|
| 7.109 | OCHF₂ | H | 2 | 2,4-dichlorophenyl | CH | |
| 7.110 | OCHF₂ | H | 0 | CH₂COOH | CH | |
| 7.111 | OCHF₂ | H | 0 | CH₂COOCH₃ | CH | |
| 7.112 | OCHF₂ | H | 0 | CH₂CON(CH₃)₂ | CH | |
| 7.113 | OCHF₂ | H | 0 | 4-Chlorophenyl | N | |
| 7.114 | OCHF₂ | H | 0 | p-tolyl | N | |
| 7.115 | OCHF₂ | furyl-2- | 0 | 2-hydroxy-carbonylphenyl | CH | |
| 7.116 | OCHF₂ | furyl-2- | 0 | 2-methoxy-carbonylphenyl | CH | |
| 7.117 | OCHF₂ | furyl-2- | 0 | phenyl | CH | |
| 7.118 | OCHF₂ | 4-chloro-phenyl | 0 | 2-hydroxy-carbonylphenyl | CH | |
| 7.119 | OCHF₂ | 4-chloro-phenyl | 0 | phenyl | CH | |
| 7.120 | OCHF₂ | CH₃ | 0 | 4-chlorophenyl | CH | |
| 7.121 | Cl | H | 2 | p-tolyl | CH | |
| 7.122 | Cl | H | 0 | p-tolyl | CH | |
| 7.123 | Cl | H | 2 | 4-chlorophenyl | CH | |
| 7.124 | Cl | H | 0 | 4-chlorophenyl | CH | |
| 7.125 | Cl | H | 0 | acetyl | CH | |
| 7.126 | Cl | H | 0 | benzoyl | CH | |
| 7.127 | Cl | H | 2 | CH₃ | CH | |
| 7.128 | Cl | H | 2 | CH₂CH₂CH₂CH₃ | CH | |
| 7.129 | Cl | H | 2 | CH(CH₃)₂ | CH | |
| 7.130 | Cl | H | 2 | benzyl | CH | |
| 7.131 | Cl | H | 2 | phenyl | CH | |
| 7.132 | Cl | H | 0 | phenyl | CH | |
| 7.133 | Cl | H | 2 | 4-bromophenyl | CH | |
| 7.134 | Cl | H | 0 | 4-bromophenyl | CH | |
| 7.135 | Cl | H | 2 | 2-chlorophenyl | CH | |
| 7.136 | Cl | H | 0 | 2-chloropehnyl | CH | |
| 7.137 | Cl | H | 0 | CH₃CH | | |
| 7.138 | Cl | H | 0 | CH₂CH₂CH₂CH₃ | CH | |
| 7.139 | Cl | H | 0 | CH(CH₃)₂ | CH | |
| 7.140 | Cl | H | 0 | benzyl | CH | |
| 7.141 | Cl | H | 2 | β-naphthyl | CH | |
| 7.142 | Cl | H | 0 | β-naphthyl | CH | 156–158° dec. |
| 7.143 | Cl | H | 2 | 1,2,4-trichloro-phenyl | CH | |
| 7.144 | Cl | H | 0 | 1,2,4-trichloro-phenyl | CH | |
| 7.145 | Cl | H | 2 | α-naphthyl | CH | |
| 7.146 | Cl | H | 2 | α-naphthyl | CH | |
| 7.147 | Cl | H | 0 | —CH₂COOCH₃ | CH | |
| 7.148 | Cl | H | 2 | 4-fluorophenyl | CH | |
| 7.149 | Cl | H | 0 | 4-fluorophenyl | CH | |
| 7.150 | Cl | H | 0 | 4-nitrophenyl | CH | |
| 7.151 | Cl | H | 0 | 4-nitrophenyl | CH | |
| 7.152 | Cl | H | 2 | 2-nitrophenyl | CH | |
| 7.153 | Cl | H | 0 | 2-nitrophenyl | CH | |
| 7.154 | Cl | H | 2 | 2-trifluoromethyl | CH | |
| 7.155 | Cl | H | 0 | 2-trifluoromethyl | CH | |
| 7.156 | Cl | H | 2 | 4-methoxyphenyl | CH | |
| 7.157 | Cl | H | 0 | 4-methoxyphenyl | CH | |
| 7.158 | Cl | H | 2 | 2-methoxyphenyl | CH | |
| 7.159 | Cl | H | 0 | 2-methoxyphenyl | CH | |
| 7.160 | Cl | H | 2 | 2,4,6-trimethyl-phenyl | CH | |
| 7.161 | Cl | H | 0 | 2,4,6-trimethyl-phenyl | CH | |
| 7.162 | Cl | H | 0 | CS—N(CH₃)₂ | CH | |
| 7.163 | Cl | H | 0 | CSN(CH₂CH₃)₂ | CH | |
| 7.164 | Cl | H | 0 | CSN(CH₂CH₃)₂ | CH | |
| 7.165 | Cl | H | 0 | pyrrolidinothio-carbonyl | CH | |
| 7.166 | Cl | H | 0 | piperidinothio-carbonyl | CH | |
| 7.167 | Cl | H | 0 | N-phenylcarbamoyl-methyl | CH | |
| 7.168 | Cl | H | 0 | 2,4-dichlorophenyl | CH | |

TABLE 7-continued

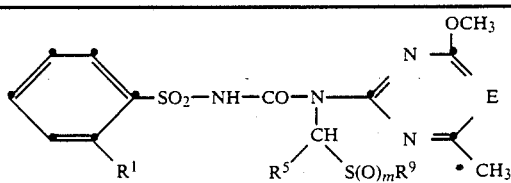

| No | R¹ | R⁵ | m | R⁹ | E | m.p.(°C.) |
|---|---|---|---|---|---|---|
| 7.169 | Cl | H | 2 | 2,4-dichlorophenyl | CH | |
| 7.170 | Cl | H | 0 | CH₂COOH | CH | |
| 7.171 | Cl | H | 0 | CH₂COOCH₃ | CH | |
| 7.172 | Cl | H | 0 | CH₂CON(CH₃)₂ | CH | |
| 7.173 | Cl | H | 0 | 4-chlorophenyl | N | |
| 7.174 | Cl | H | 0 | p-tolyl | N | |
| 7.175 | Cl | furyl-2- | 0 | 2-hydroxy-carbonylphenyl | CH | |
| 7.176 | Cl | furyl-2- | 0 | 2-methoxy-carbonylphenyl | CH | |
| 7.177 | Cl | furyl-2- | 0 | phenyl | CH | |
| 7.178 | Cl | 4-chloro-phenyl | 0 | 2-hydroxy-carbonylphenyl | CH | |
| 7.179 | Cl | 4-chloro-phenyl | 0 | phenyl | CH | |
| 7.180 | Cl | CH₃ | 0 | 4-chlorophenyl | CH | |
| 7.181 | OCH₃ | H | 0 | phenyl | CH | |
| 7.182 | OCH₃ | H | 2 | phenyl | CH | |
| 7.183 | OCH₃ | H | 0 | CSN(CH₃)₂ | CH | |
| 7.184 | OCH₃ | H | 0 | pyrrolidinothio-carbonyl | CH | |
| 7.185 | OCH₃ | H | 0 | CH₃ | CH | |
| 7.186 | OCH₃ | H | 2 | CH₃ | CH | |
| 7.187 | NO₂ | H | 0 | phenyl | CH | |
| 7.188 | NO₂ | H | 2 | phenyl | CH | |
| 7.189 | NO₂ | H | 0 | CSN(CH₃)₂ | CH | |
| 7.190 | NO₂ | H | 0 | pyrrolidinothio-carbonyl | CH | |
| 7.191 | NO₂ | H | 0 | CH₃ | CH | |
| 7.192 | NO₂ | H | 2 | CH₃ | CH | |
| 7.193 | CF₃ | H | 0 | phenyl | CH | |
| 7.194 | CF₃ | H | 2 | phenyl | CH | |
| 7.195 | CF₃ | H | 0 | CSN(CH₃)₂ | CH | |
| 7.196 | CF₃ | H | 0 | pyrrolidino-thiocarbonyl | CH | |
| 7.197 | CF₃ | H | 0 | CH₃ | CH | |
| 7.198 | CF₃ | H | 2 | CH₃ | CH | |
| 7.199 | OSO₂CH₃ | H | 0 | phenyl | CH | |
| 7.200 | OSO₂CH₃ | H | 2 | phenyl | CH | |
| 7.201 | OSO₂CH₃ | H | 0 | CSN(CH₃)₂ | CH | |
| 7.202 | OSO₂CH₃ | H | 0 | pyrrolidino-thiocarbonyl | CH | |
| 7.203 | OSO₂CH₃ | H | 0 | CH₃ | CH | |
| 7.204 | OSO₂CH₃ | H | 2 | CH₃ | CH | |
| 7.205 | OSO₂C₃H₇n | H | 2 | phenyl | CH | |
| 7.206 | OSO₂C₃H₇n | H | 2 | phenyl | CH | |
| 7.207 | OSO₂C₃H₇n | H | 0 | CSN(CH₃)₂ | CH | |
| 7.208 | OSO₂C₃H₇n | H | 0 | pyrrolidino-thiocarbonyl | CH | |
| 7.209 | OSO₂C₃H₇n | H | 2 | CH₃ | CH | |
| 7.210 | OSO₂C₃H₇n | H | 0 | CH₃ | CH | |
| 7.211 | SO₂N(CH₃)₂ | H | 0 | phenyl | CH | |
| 7.212 | SO₂N(CH₃)₂ | H | 2 | phenyl | CH | |
| 7.213 | SO₂N(CH₃)₂ | H | 0 | CSN(CH₃)₂ | CH | |
| 7.214 | SO₂N(CH₃)₂ | H | 0 | pyrrolidino-thiocarbonyl | CH | |
| 7.215 | SO₂N(CH₃)₂ | H | 0 | CH₃ | CH | |
| 7.216 | SO₂N(CH₃)₂ | H | 2 | CH₃ | CH | |
| 7.217 | CH₃ | H | 0 | phenyl | CH | |
| 7.218 | CH₃ | H | 2 | phenyl | CH | |
| 7.219 | CH₃ | H | 0 | CSN(CH₃)₂ | CH | |
| 7.220 | CH₃ | H | 0 | pyrrolidino-thiocarbonyl | CH | |
| 7.221 | CH₃ | H | 0 | CH₃ | CH | |
| 7.222 | CH₃ | H | 2 | CH₃ | CH | |
| 7.223 | SO₂CH₃ | H | 0 | phenyl | CH | |
| 7.224 | SO₂CH₃ | H | 2 | phenyl | CH | |
| 7.225 | SO₂CH₃ | H | 0 | CSN(CH₃)₂ | CH | |
| 7.226 | SO₂CH₃ | H | 0 | pyrrolidino-thiocarbonyl | CH | |
| 7.227 | SO₂CH₃ | H | 0 | CH₃ | CH | |
| 7.228 | SO₂CH₃ | H | 2 | CH₃ | CH | |

TABLE 7-continued

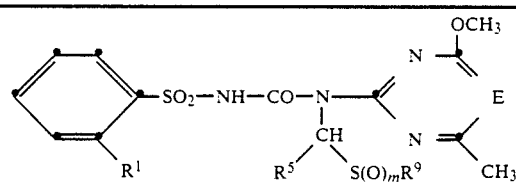

| No | R¹ | R⁵ | m | R⁹ | E | m.p.(°C.) |
|---|---|---|---|---|---|---|
| 7.229 | CF₃ | H | 2 | β-naphthyl | CH | 153–156° dec. |
| 7.230 | 2,6-Cl₂ | H | 2 | β-naphthyl | CH | 154–158° dec. |
| 7.231 | phenyl | H | 2 | CH₃ | CH | 166–170° dec. |
| 7.232 | phenyl | H | 2 | p-tolyl | CH | 156–159° dec. |
| 7.233 | phenyl | H | 0 | 4-chlorophenyl | CH | 161–154° |
| 7.234 | F | H | 0 | 4-chlorophenyl | CH | 126–127° |
| 7.235 | phenyl | H | 0 | CH₂COOCH₃ | CH | 127–129° |
| 7.236 | NO₂ | H | 0 | anilidocarbonyl-methyl | CH | 162–165° (dec.) |
| 7.237 | 2-Cl,6-CH₃ | H | 2 | p-tolyl | CH | 150–152° (dec.) |

TABLE 8

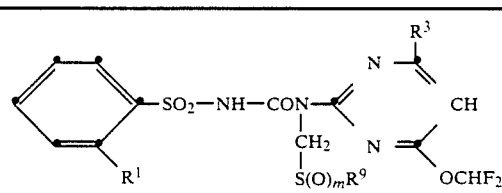

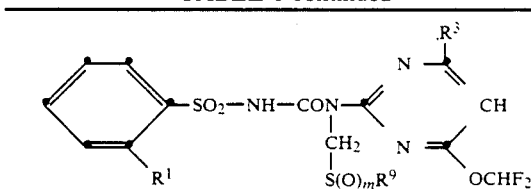

| NO | R¹ | m | R⁹ | R³ | m.p. (°C.) |
|---|---|---|---|---|---|
| 8.001 | COOCH₃ | 0 | p-tolyl | CH₃ | |
| 8.002 | COOCH₃ | 0 | p-tolyl | OCH₃ | |
| 8.003 | COOCH₃ | 0 | p-tolyl | OCHF₂ | |
| 8.004 | COOCH₃ | 2 | p-tolyl | CH₃ | |
| 8.005 | COOCH₃ | 2 | p-tolyl | OCH₃ | |
| 8.006 | COOCH₃ | 2 | p-tolyl | OCHF₂ | |
| 8.007 | COOCH₃ | 0 | CSN(CH₃)₂ | CH₃ | |
| 8.008 | COOCH₃ | 0 | CSN(CH₃)₂ | OCH₃ | |
| 8.009 | COOCH₃ | 0 | CSN(CH₃)₂ | OCHF₂ | |
| 8.010 | COOCH₃ | 2 | ethyl | CH₃ | |
| 8.011 | COOCH₃ | 2 | ethyl | OCH₃ | |
| 8.012 | COOCH₃ | 2 | ethyl | OCHF₂ | |
| 8.013 | COOCH₃ | 0 | 4-chlorophenyl | CH₃ | |
| 8.014 | COOCH | 0 | 4-chlorophenyl | OCHF₂ | |
| 8.015 | COOCH₃ | 0 | 4-chlorophenyl | OCH₃ | |
| 8.016 | COOCH₃ | 2 | 4-chlorophenyl | CH₃ | |
| 8.017 | COOCH₃ | 2 | 4-chlorophenyl | OCHF₂ | |
| 8.018 | COOCH₃ | 2 | 4-chlorophenyl | OCH₃ | |
| 8.019 | COOCH₃ | 0 | pyrrolidino thiocarbonyl | CH₃ | |
| 8.020 | COOCH₃ | 0 | pyrrolidino-thiocarbonyl | OCH₂ | |
| 8.021 | COOCH₃ | 0 | pyrrolidino-thiocarbonyl | OCHF₂ | |
| 8.022 | OCHF₂ | 0 | p-tolyl | CH₃ | |
| 8.023 | OCHF₂ | 0 | p-tolyl | OCH₃ | |
| 8.024 | OCHF₂ | 0 | p-tolyl | OCHF₂ | |
| 8.025 | OCHF₂ | 2 | p-tolyl | CH₃ | 154–158° dec. |
| 8.026 | OCHF₂ | 2 | p-tolyl | OCH₃ | |
| 8.027 | OCHF₂ | 2 | p-tolyl | OCHF₂ | |
| 8.028 | OCHF₂ | 0 | CSN(CH₃)₂ | CH₃ | |
| 8.029 | OCHF₂ | 0 | CSN(CH₃)₂ | OCH₃ | |
| 8.030 | OCHF₂ | 0 | CSN(CH₃)₂ | OCHF₂ | |
| 8.031 | OCHF₂ | 2 | ethyl | CH₃ | |
| 8.032 | OCHF₂ | 2 | ethyl | OCH₃ | |
| 8.033 | OCHF₂ | 2 | ethyl | OCHF₂ | |
| 8.034 | OCHF₂ | 0 | 4-chlorophenyl | CH₃ | |
| 8.035 | OCHF₂ | 0 | 4-chlorophenyl | OCH₃ | |
| 8.036 | OCHF₂ | 0 | 4-chlorophenyl | OCH₃ | |
| 8.037 | OCHF₂ | 2 | 4-chlorophenyl | CH₃ | |
| 8.038 | OCHF₂ | 2 | 4-chlorophenyl | OCHF₂ | |
| 8.039 | OCHF₂ | 2 | 4-chlorophenyl | OCH₃ | |
| 8.040 | OCHF₂ | 0 | pyrrolidino thiocarbonyl | CH₃ | |
| 8.041 | OCHF₂ | 0 | pyrrolidino-thiocarbonyl | OCH₂ | |
| 8.042 | OCHF₂ | 0 | pyrrolidino-thiocarbonyl | OCHF₂ | |
| 8.043 | Cl | 0 | p-tolyl | CH₃ | |
| 8.044 | Cl | 0 | p-tolyl | OCH₃ | |
| 8.045 | Cl | 0 | p-tolyl | OCHF₂ | |
| 8.046 | Cl | 2 | p-tolyl | CH₃ | |
| 8.047 | Cl | 2 | p-tolyl | OCH₃ | |
| 8.048 | Cl | 2 | p-tolyl | OCHF₂ | |
| 8.049 | Cl | 0 | CSN(CH₃)₂ | CH₃ | |
| 8.050 | Cl | 0 | CSN(CH₃)₂ | OCH₃ | |
| 8.051 | Cl | 0 | CSN(CH₃)₂ | OCHF₂ | |
| 8.052 | Cl | 2 | ethyl | CH₃ | |
| 8.053 | Cl | 2 | ethyl | OCH₃ | |
| 8.054 | Cl | 2 | ethyl | OCHF₂ | |
| 8.055 | Cl | 0 | 4-chlorophenyl | CH₃ | |
| 8.056 | Cl | 0 | 4-chlorophenyl | OCHF₂ | |
| 8.057 | Cl | 0 | 4-chlorophenyl | OCH₃ | |
| 8.058 | Cl | 2 | 4-chlorophenyl | CH₃ | |
| 8.059 | Cl | 2 | 4-chlorophenyl | OCHF₂ | |
| 8.060 | Cl | 2 | 4-chlorophenyl | OCH₃ | |
| 8.061 | Cl | 0 | pyrrolidino-thiocarbonyl | CH₃ | |
| 8.062 | Cl | 0 | pyrrolidino-thiocarbonyl | OCH₂ | |
| 8.063 | Cl | 0 | pyrrolidino-thiocarbonyl | OCHF₂ | |
| 8.064 | NO₂ | 0 | p-tolyl | CH₃ | |
| 8.065 | NO₂ | 0 | p-tolyl | OCH₃ | |
| 8.066 | NO₂ | 0 | p-tolyl | OCHF₂ | |
| 8.067 | NO₂ | 2 | p-tolyl | CH₃ | |
| 8.068 | NO₂ | 2 | p-tolyl | OCH₃ | |
| 8.069 | NO₂ | 2 | p-tolyl | OCHF₂ | |
| 8.070 | NO₂ | 0 | CSN(CH₃)₂ | CH₃ | |
| 8.071 | NO₂ | 0 | CSN(CH₃)₂ | OCH₃ | |
| 8.072 | NO₂ | 0 | CSN(CH₃)₂ | OCHF₂ | |
| 8.073 | NO₂ | 2 | ethyl | CH₃ | |
| 8.074 | NO₂ | 2 | ethyl | OCH₃ | |

TABLE 8-continued

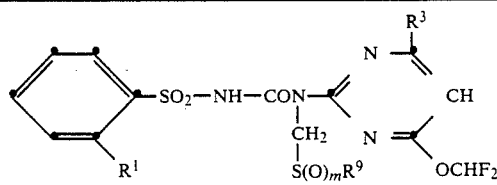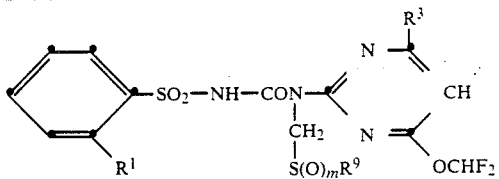

| NO | R¹ | m | R⁹ | R³ | m.p. (°C.) |
|---|---|---|---|---|---|
| 8.075 | $NO_2$ | 2 | ethyl | $OCHF_2$ | |
| 8.076 | $NO_2$ | 0 | 4-chlorophenyl | $CH_3$ | |
| 8.077 | $NO_2$ | 0 | 4-chlorophenyl | $OCHF_2$ | |
| 8.078 | $NO_2$ | 0 | 4-chlorophenyl | $OCH_3$ | |
| 8.079 | $NO_2$ | 2 | 4-chlorophenyl | $CH_3$ | |
| 8.080 | $NO_2$ | 2 | 4-chlorophenyl | $OCHF_2$ | |
| 8.081 | $NO_2$ | 2 | 4-chlorophenyl | $OCH_3$ | |
| 8.082 | $NO_2$ | 0 | pyrrolidino-thiocarbonyl | $CH_3$ | |
| 8.083 | $NO_2$ | 0 | pyrrolidino-thiocarbonyl | $OCH_2$ | |
| 8.084 | $NO_2$ | 0 | pyrrolidino-thiocarbonyl | $OCHF_2$ | |
| 8.085 | $COOCH_3$ | 0 | $CH_3$ | $CH_3$ | |
| 8.086 | $COOCH_3$ | 0 | $CH_3$ | $OCH_3$ | |
| 8.087 | $COOCH_3$ | 0 | $CH_3$ | $OCHF_2$ | |
| 8.088 | $COOCH_3$ | 2 | $CH_3$ | $CH_3$ | |
| 8.089 | $COOCH_3$ | 2 | $CH_3$ | $OCH_3$ | |
| 8.090 | $COOCH_3$ | 2 | $CH_3$ | $OCHF_2$ | |
| 8.091 | $OCHF_2$ | 0 | $CH_3$ | $CH_3$ | |
| 8.092 | $OCHF_2$ | 0 | $CH_3$ | $OCHF_2$ | |
| 8.093 | $OCHF_2$ | 0 | $CH_3$ | $OCH_3$ | |
| 8.094 | $OCHF_2$ | 2 | $CH_3$ | $CH_3$ | |
| 8.095 | $OCHF_2$ | 2 | $CH_3$ | $OCH_3$ | |
| 8.096 | $OCHF_2$ | 2 | $CH_3$ | $OCHF_2$ | |
| 8.097 | $NO_2$ | 2 | $CH_2COOH$ | $CH_3$ | 139–141° (dec.) |
| 8.098 | $OCH_3$ | 2 | $CH_3$ | $CH_3$ | 148° (dec.) |
| 8.099 | $CF_3$ | 2 | $CH_3$ | $CH_3$ | 159–160° (dec.) |

TABLE 9

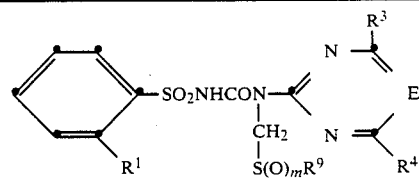

| No | R¹ | m | R⁹ | R³ | R⁴ | E | m.p. (°C.) |
|---|---|---|---|---|---|---|---|
| 9.001 | $COOCH_3$ | 0 | pyrrolidino-thiocarbonyl | $CH_2OCH_3$ | $OCH_3$ | CH | |
| 9.002 | $COOCH_3$ | 0 | pyrrolidino-thiocarbonyl | $OCH_2CH_3$ | $CH_3$ | CH | |
| 9.003 | $COOCH_3$ | 0 | pyrrolidino-thiocarbonyl | Cl | $OCH_3$ | CH | |
| 9.004 | $COOCH_3$ | 0 | pyrrolidino-thiocarbonyl | $N(CH_3)_2$ | $OCH_3$ | CH | |
| 9.005 | $COOCH_3$ | 0 | pyrrolidino-thiocarbonyl | $CH(OCH_3)_2$ | $OCH_3$ | CH | |
| 9.006 | $COOCH_3$ | 0 | pyrrolidino-thiocarbonyl | $CH_2Cl$ | $OCH_3$ | CH | |
| 9.007 | $COOCH_3$ | 0 | dimethylthio-carbamoyl | $CH_2OCH_3$ | $OCH_3$ | CH | |
| 9.008 | $COOCH_3$ | 0 | dimethylthio-carbamoyl | $OCH_2CH_3$ | $CH_3$ | CH | |
| 9.009 | $COOCH_3$ | 0 | dimethylthio-carbamoyl | Cl | $OCH_3$ | CH | |
| 9.010 | $COOCH_3$ | 0 | dimethylthio-carbamoyl | $N(CH_3)_2$ | $OCH_3$ | CH | |
| 9.011 | $COOCH_3$ | 0 | dimethylthio-carbamoyl | $CH(OCH_3)$ | $OCH_3$ | CH | |
| 9.012 | $COOCH_3$ | 0 | benzoyl | $CH_2OCH_3$ | $OCH_3$ | CH | |
| 9.013 | $COOCH_3$ | 0 | benzoyl | $OCH_2CH_3$ | $CH_3$ | CH | |
| 9.014 | $COOCH_3$ | 0 | benzoyl | Cl | $OCH_3$ | N | |
| 9.015 | $COOCH_3$ | 0 | benzoyl | $N(CH_3)_2$ | $OCH_3$ | N | |
| 9.016 | $COOCH_3$ | 0 | benzoyl | $CH(OCH_3)_2$ | $OCH_3$ | CH | |
| 9.017 | $COOCH_3$ | 0 | benzoyl | $CH_2Cl$ | $OCH_3$ | CH | |
| 9.018 | $COOCH_3$ | 0 | acetyl | $CH_2OCH_3$ | $OCH_3$ | CH | |
| 9.019 | $COOCH_3$ | 0 | acetyl | $OCH_2CH_3$ | $CH_3$ | CH | |
| 9.020 | $COOCH_3$ | 0 | acetyl | Cl | $OCH_3$ | N | |
| 9.021 | $COOCH_3$ | 0 | acetyl | $N(CH_3)_2$ | $OCH_3$ | N | |
| 9.022 | $COOCH_3$ | 0 | acetyl | $CH(OCH_3)_2$ | $OCH_3$ | CH | |
| 9.023 | $COOCH_3$ | 0 | acetyl | $CH_2Cl$ | $OCH_3$ | CH | |
| 9.024 | $OCHF_2$ | 0 | pyrrolidino-thiocarbonyl | $CH_2OCH_3$ | $OCH_3$ | CH | |
| 9.025 | $OCHF_2$ | 0 | pyrrolidino-thiocarbonyl | $OCH_2CH_3$ | $CH_3$ | CH | |
| 9.026 | $OCHF_2$ | 0 | pyrrolidino-thiocarbonyl | Cl | $OCH_3$ | CH | 143–144° dec. |

TABLE 9-continued

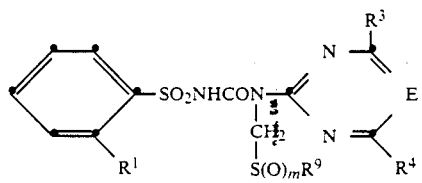

| No | R¹ | m | R⁹ | R³ | R⁴ | E | m.p. (°C.) |
|---|---|---|---|---|---|---|---|
| 9.027 | OCHF₂ | 0 | pyrrolidino-thiocarbonyl | N(CH₃)₂ | OCH₃ | CH | |
| 9.028 | OCHF₂ | 0 | pyrrolidino-thiocarbonyl | CH(OCH₃)₂ | OCH₃ | CH | |
| 9.029 | OCHF₂ | 0 | pyrrolidino-thiocarbonyl | CH₂Cl | OCH₃ | CH | |
| 9.030 | OCHF₂ | 0 | dimethylthio-carbamoyl | CH₂OCH₃ | OCH₃ | CH | |
| 9.031 | OCHF₂ | 0 | dimethylthio-carbamoyl | OCH₂CH₃ | CH₃ | CH | |
| 9.032 | OCHF₂ | 0 | dimethylthio-carbamoyl | Cl | OCH₃ | N | |
| 9.033 | OCHF₂ | 0 | dimethylthio-carbamoyl | N(CH₃)₂ | OCH₃ | N | |
| 9.034 | OCHF₂ | 0 | dimethylthio-carbamoyl | CH(OCH₃) | OCH₃ | CH | |
| 9.035 | OCHF₂ | 0 | benzoyl | CH₂OCH₃ | OCH₃ | CH | |
| 9.036 | OCHF₂ | 0 | benzoyl | OCH₂CH₃ | CH₃ | CH | |
| 9.037 | OCHF₂ | 0 | benzoyl | Cl | OCH₃ | N | |
| 9.038 | OCHF₂ | 0 | benzoyl | N(CH₃)₂ | OCH₃ | CH | |
| 9.039 | OCHF₂ | 0 | benzoyl | CH(OCH₃)₂ | OCH₃ | CH | |
| 9.040 | OCHF₂ | 0 | benzoyl | CH₂Cl | OCH₃ | CH | |
| 9.041 | OCHF₂ | 0 | acetyl | CH₂OCH₃ | OCH₃ | CH | |
| 9.042 | OCHF₂ | 0 | acetyl | OCH₂CH₃ | CH₃ | CH | |
| 9.043 | OCHF₂ | 0 | acetyl | Cl | OCH₃ | CH | |
| 9.044 | OCHF₂ | 0 | acetyl | N(CH₃)₂ | OCH₃ | N | |
| 9.045 | OCHF₂ | 0 | acetyl | CH(OCH₃)₂ | OCH₃ | CH | |
| 9.046 | OCHF₂ | 0 | acetyl | CH₂Cl | OCH₃ | CH | |
| 9.047 | Cl | 0 | pyrrolidino-thiocarbonyl | CH₂OCH₃ | OCH₃ | CH | |
| 9.048 | Cl | 0 | pyrrolidino-thiocarbonyl | OCH₂CH₃ | CH₃ | CH | |
| 9.049 | Cl | 0 | pyrrolidino-thiocarbonyl | Cl | OCH₃ | CH | 141–143° dec. |
| 9.050 | Cl | 0 | pyrrolidino thiocarbonyl | N(CH₃)₂ | OCH₃ | N | |
| 9.051 | Cl | 0 | pyrrolidino-thiocarbonyl | CH(OCH₃)₂ | OCH₃ | CH | |
| 9.052 | Cl | 0 | pyrrolidino-thiocarbonyl | CH₂Cl | OCH₃ | CH | |
| 9.053 | Cl | 0 | dimethylthio-carbamoyl | CH₂OCH₃ | OCH₃ | CH | |
| 9.054 | Cl | 0 | dimethylthio-carbamoyl | OCH₂CH₃ | CH₃ | CH | |
| 9.055 | Cl | 0 | dimethylthio-carbamoyl | Cl | OCH₃ | CH | |
| 9.056 | Cl | 0 | dimethylthio-carbamoyl | N(CH₃)₂ | OCH₃ | CH | |
| 9.057 | Cl | 0 | dimethylthio-carbamoyl | CH(OCH₃)₂ | OCH₃ | CH | |
| 9.058 | Cl | 0 | benzoyl | CH₂OCH₃ | OCH₃ | CH | |
| 9.059 | Cl | 0 | benzoyl | OCH₂CH₃ | CH₃ | CH | |
| 9.060 | Cl | 0 | benzoyl | Cl | OCH₃ | N | |
| 9.061 | Cl | 0 | benzoyl | N(CH₃)₂ | OCH₃ | CH | |
| 9.062 | Cl | 0 | benzoyl | CH(OCH₃)₂ | OCH₃ | CH | |
| 9.063 | Cl | 0 | benzoyl | CH₂Cl | OCH₃ | CH | |
| 9.064 | Cl | 0 | acetyl | CH₂OCH₃ | OCH₃ | CH | |
| 9.065 | Cl | 0 | acetyl | OCH₂CH₃ | CH₃ | CH | |
| 9.066 | Cl | 0 | acetyl | Cl | OCH₃ | CH | |
| 9.067 | Cl | 0 | acetyl | N(CH₃)₂ | OCH₃ | N | |
| 9.068 | Cl | 0 | acetyl | CH(OCH₃)₂ | OCH₃ | CH | |
| 9.069 | Cl | 0 | acetyl | CH₂Cl | OCH₃ | CH | |
| 9.070 | COOCH₃ | 0 | 2-chlorophenyl | CH₂CH₃ | OCH₃ | CH | |
| 9.071 | COOCH₃ | 2 | 2-chlorophenyl | CH₂CH₃ | OCH₃ | CH | |
| 9.072 | COOCH₃ | 0 | 2-chlorophenyl | Cl | OCH₃ | N | |
| 9.073 | COOCH₃ | 2 | 2-chlorophenyl | Cl | OCH₃ | CH | |
| 9.074 | COOCH₃ | 0 | 2-chlorophenyl | N(CH₃)₂ | OCH₃ | N | |
| 9.075 | COOCH₃ | 2 | 2-chlorophenyl | N(CH₃)₂ | OCH₃ | CH | |
| 9.076 | COOCH₃ | 0 | CH₂CH₃ | Cl | OCH₃ | N | |
| 9.077 | COOCH₃ | 2 | CH₂CH₃ | Cl | OCH₃ | CH | |
| 9.078 | COOCH₃ | 0 | CH₂CH₃ | CH₂OCH₃ | OCH₃ | CH | |

TABLE 9-continued

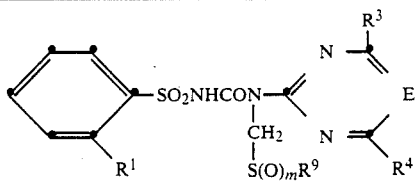

| No | R¹ | m | R⁹ | R³ | R⁴ | E | m.p. (°C.) |
|---|---|---|---|---|---|---|---|
| 9.079 | COOCH₃ | 2 | CH₂CH₃ | CH₂OCH₃ | OCH₃ | CH | |
| 9.080 | COOCH₃ | 0 | p-tolyl | OCH₃ | Cl | CH | |
| 9.081 | COOCH₃ | 2 | p-tolyl | OCH₃ | Cl | N | |
| 9.082 | COOCH₃ | 0 | p-tolyl | CH₂OCH₃ | OCH₃ | CH | |
| 9.083 | COOCH₃ | 2 | p-tolyl | CH₂OCH₃ | OCH₃ | CH | |
| 9.084 | OCHF₂ | 0 | p-tolyl | CH₂OCH₃ | OCH₃ | CH | |
| 9.085 | OCHF₂ | 2 | p-tolyl | CH₂OCH₃ | OCH₃ | CH | 154–157° dec. |
| 9.086 | COOCH₃ | 0 | methyl | CH₂OCH₃ | CH₃ | CH | |
| 9.087 | COOCH₃ | 0 | methyl | OCH₂CH₃ | OCH₃ | CH | |
| 9.088 | COOCH₃ | 0 | methyl | Cl | OCH₃ | CH | |
| 9.089 | COOCH₃ | 0 | methyl | N(CH₃)₂ | OCH₃ | CH | |
| 9.090 | COOCH₃ | 0 | methyl | CH(OCH₃)₂ | OCH₃ | CH | |
| 9.091 | COOCH₃ | 0 | methyl | CH₂Cl | OCH₃ | CH | |
| 9.092 | COOCH₃ | 2 | methyl | CH₂OCH₃ | CH₃ | CH | |
| 9.093 | COOCH₃ | 2 | methyl | OCH₂CH₃ | CH₃ | CH | |
| 9.094 | COOCH₃ | 2 | methyl | Cl | OCH₃ | N | |
| 9.095 | COOCH₃ | 2 | methyl | N(CH₃)₂ | OCH₃ | N | |
| 9.096 | COOCH₃ | 2 | methyl | CH(OCH₃) | OCH₃ | CH | |
| 9.097 | COOCH₃ | 0 | 4-chlorophenyl | CH₂OCH₃ | CH₃ | CH | |
| 9.098 | COOCH₃ | 0 | 4-chlorophenyl | OCH₂CH₃ | CH₃ | CH | |
| 9.099 | COOCH₃ | 0 | 4-chlorophenyl | Cl | OCH₃ | N | |
| 9.100 | COOCH₃ | 0 | 4-chlorophenyl | N(CH₃)₂ | OCH₃ | N | |
| 9.101 | COOCH₃ | 0 | 4-chlorophenyl | CH(OCH₃)₂ | OCH₃ | CH | |
| 9.102 | COOCH₃ | 0 | 4-chlorophenyl | CH₂Cl | OCH₃ | CH | |
| 9.103 | COOCH₃ | 2 | 4-chlorophenyl | CH₂OCH₃ | CH₃ | CH | |
| 9.104 | COOCH₃ | 2 | 4-chlorophenyl | OCH₂CH₃ | CH₃ | CH | |
| 9.105 | COOCH₃ | 2 | 4-chlorophenyl | Cl | OCH₃ | N | |
| 9.106 | COOCH₃ | 2 | 4-chlorophenyl | N(CH₃)₂ | OCH₃ | N | |
| 9.107 | COOCH₃ | 2 | 4-chlorophenyl | CH(OCH₃)₂ | OCH₃ | CH | |
| 9.108 | COOCH₃ | 2 | 4-chlorophenyl | CH₂Cl | OCH₃ | CH | |
| 9.109 | OCHF₂ | 0 | methyl | CH₂OCH₃ | CH₃ | CH | |
| 9.110 | OCHF₂ | 0 | methyl | OCH₂CH₃ | OCH₃ | CH | |
| 9.111 | OCHF₂ | 0 | methyl | Cl | OCH₃ | N | |
| 9.112 | OCHF₂ | 0 | methyl | N(CH₃)₂ | OCH₃ | CH | |
| 9.113 | OCHF₂ | 0 | methyl | CH(OCH₃)₂ | OCH₃ | CH | |
| 9.114 | OCHF₂ | 0 | methyl | CH₂Cl | OCH₃ | CH | |
| 9.115 | OCHF₂ | 2 | methyl | CH₂OCH₃ | CH₃ | CH | |
| 9.116 | OCHF₂ | 2 | methyl | OCH₂CH₃ | CH₃ | CH | |
| 9.117 | OCHF₂ | 2 | methyl | Cl | OCH₃ | N | |
| 9.118 | OCHF₂ | 2 | methyl | N(CH₃)₂ | OCH₃ | N | |
| 9.119 | OCHF₂ | 2 | methyl | CH(OCH₃) | OCH₃ | CH | |
| 9.120 | OCHF₂ | 0 | 4-chlorophenyl | CH₂OCH₃ | CH₃ | CH | |
| 9.121 | OCHF₂ | 0 | 4-chlorophenyl | OCH₂CH₃ | CH₃ | CH | |
| 9.122 | OCHF₂ | 0 | 4-chlorophenyl | Cl | OCH₃ | N | |
| 9.123 | OCHF₂ | 0 | 4-chlorophenyl | N(CH₃)₂ | OCH₃ | N | |
| 9.124 | OCHF₂ | 0 | 4-chlorophenyl | CH(OCH₃)₂ | OCH₃ | CH | |
| 9.125 | OCHF₂ | 0 | 4-chlorophenyl | CH₂Cl | OCH₃ | CH | |
| 9.126 | OCHF₂ | 2 | 4-chlorophenyl | CH₂OCH₃ | CH₃ | CH | |
| 9.127 | OCHF₂ | 2 | 4-chlorophenyl | OCH₂CH₃ | CH₃ | CH | |
| 9.128 | OCHF₂ | 2 | 4-chlorophenyl | Cl | OCH₃ | N | |
| 9.129 | OCHF₂ | 2 | 4-chlorophenyl | N(CH₃)₂ | OCH₃ | N | |
| 9.130 | OCHF₂ | 2 | 4-chlorophenyl | CH(OCH₃)₂ | OCH₃ | CH | |
| 9.131 | OCHF₂ | 2 | 4-chlorophenyl | CH₂Cl | OCH₃ | CH | |
| 9.132 | Cl | 0 | 4-chlorophenyl | Cl | OCH₃ | CH | 142–144° |
| 9.133 | Cl | 2 | 4-chlorophenyl | Cl | OCH₃ | CH | 140–142° dec. |
| 9.134 | COOC₂H₅ | 0 | p-tolyl | Cl | OCH₃ | CH | |
| 9.135 | COOC₂H₅ | 2 | p-tolyl | Cl | OCH₃ | CH | |
| 9.136 | COOCH₃ | 0 | 2,4,5-trichlorophenyl | CH₂OCH₃ | OCH₃ | CH | 128–130° dec. |
| 9.137 | COOCH₃ | 0 | p-tolyl | N(CH₃)₂ | OCH₃ | N | 138–140° |
| 9.138 | F | 0 | CH₂COOCH₃ | N(CH₃)₂ | OCH₃ | N | 130–133° |
| 9.139 | NO₂ | 0 | 2,4,5-trichlorophenyl | CH₂OCH₃ | OCH₃ | CH | 118–120° |
| 9.140 | Cl | 0 | CH₂COOCH₃ | N(CH₃)₂ | OCH₃ | N | 135–138° |
| 9.141 | COOCH₃ | 0 | CH₂COOCH₃ | N(CH₃)₂ | OCH₃ | N | 145–148° |
| 9.142 | CF₃ | 2 | CH₃ | N(CH₃)₂ | OCH₃ | N | 171–175° dec. |

TABLE 10

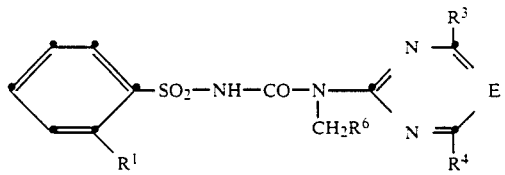

| No | R¹ | R⁶ | R³ | R⁴ | E | m.p. (°C.) |
|---|---|---|---|---|---|---|
| 10.001 | COOCH₃ | benztriazol-1-yl | CH₃ | CH₃ | CH | 178–180° |
| 10.002 | COOCH₃ | 1,2,4-triazol-1-yl | CH₃ | CH₃ | CH | 164–167° |
| 10.003 | COOCH₃ | 2-methylbenzimidazol-1-yl | CH₃ | CH₃ | CH | |
| 10.004 | COOCH₃ | 2,3-dimethylindol-1-yl | CH₃ | CH₃ | CH | |
| 10.005 | Cl | benztriazol-1-yl | CH₃ | CH₃ | CH | 122–128° dec. |
| 10.006 | Cl | 1,2,4-triazol-1-yl | CH₃ | CH₃ | CH | 152–157° dec. |
| 10.007 | Cl | 2-methylbenzimidazol-1-yl | CH₃ | CH₃ | CH | |
| 10.008 | Cl | 2,3-dimethylindol-1-yl | CH₃ | CH₃ | CH | |
| 10.009 | OCHF₂ | benztriazol-1-yl | CH₃ | CH₃ | CH | |
| 10.010 | OCHF₂ | 1,2,4-triazol-1-yl | CH₃ | CH₃ | CH | |
| 10.011 | OCHF₂ | 2-methylbenzimidazol-1-yl | CH₃ | CH₃ | CH | |
| 10.012 | OCHF₂ | 2,3-dimethylindol-1-yl | CH₃ | CH₃ | CH | |
| 10.013 | OCHF₂ | benztriazol-1-yl | CH₃ | OCHF₂ | CH | 109–111° |
| 10.014 | COOCH₃ | benztriazol-1-yl | OCH₃ | OCH₃ | CH | |
| 10.015 | COOCH₃ | 1,2,4-triazol-1-yl | OCH₃ | OCH₃ | CH | |
| 10.016 | COOCH₃ | 2-methylbenzimidazol-1-yl | OCH₃ | OCH₃ | CH | |
| 10.017 | COOCH₃ | 2,3-dimethylindol-1-yl | OCH₃ | OCH₃ | CH | |
| 10.018 | Cl | benztriazol-1-yl | OCH₃ | OCH₃ | CH | |
| 10.019 | Cl | 1,2,4-triazol-1-yl | OCH₃ | OCH₃ | CH | |
| 10.020 | Cl | 2-methylbenzimidazol-1-yl | OCH₃ | OCH₃ | CH | |
| 10.021 | Cl | 2,3-dimethylindol-1-yl | OCH₃ | OCH₃ | CH | |
| 10.022 | OCHF₂ | benztriazol-1-yl | OCH₃ | OCH₃ | CH | 144–147° |
| 10.023 | OCHF₂ | 1,2,4-triazol-1-yl | OCH₃ | OCH₃ | CH | |
| 10.024 | OCHF₂ | 2-methylbenzimidazol-1-yl | OCH₃ | OCH₃ | CH | |
| 10.025 | OCHF₂ | 2,3-dimethylindol-1-yl | OCH₃ | OCH₃ | CH | |
| 10.026 | OCHF₂ | benztriazol-1-yl | OCH₃ | OCH₃ | CH | |
| 10.027 | COOCH₃ | benztriazol-1-yl | OCH₃ | CH₃ | CH | |
| 10.028 | COOCH₃ | 1,2,4-triazol-1-yl | OCH₃ | CH₃ | CH | |
| 10.029 | COOCH₃ | 2-methylbenzimidazol-1-yl | OCH₃ | CH₃ | CH | |
| 10.030 | COOCH₃ | 2,3-dimethylindol-1-yl | OCH₃ | CH₃ | CH | |
| 10.031 | Cl | benztriazol-1-yl | OCH₃ | CH₃ | CH | |
| 10.032 | Cl | 1,2,4-triazol-1-yl | OCH₃ | CH₃ | CH | |
| 10.033 | Cl | 2-methylbenzimidazol-1-yl | OCH₃ | CH₃ | CH | |

| No | R¹ (R²) | R⁶ | R³ | R⁴ | E | m.p. (°C.) |
|---|---|---|---|---|---|---|
| 10.034 | Cl | 2,3-dimethylindol-1-yl | OCH₃ | CH₃ | CH | |
| 10.035 | OCHF₂ | benztriazol-1-yl | OCH₃ | CH₃ | CH | 154–158° |
| 10.036 | OCHF₂ | 1,2,4-triazol-1-yl | OCH₃ | CH₃ | CH | |
| 10.037 | OCHF₂ | 2-methylbenzimidazol-1-yl | OCH₃ | CH₃ | CH | |
| 10.038 | OCHF₂ | 2,3-dimethylindol-1-yl | OCH₃ | CH₃ | CH | |
| 10.039 | OCHF₂ | benztriazol-1-yl | OCH₃ | OCHF₂ | CH | |
| 10.040 | 2,6-Cl₂ | 1,2,4-triazol-1-yl | OCH₃ | OCH₃ | CH | 156–159° |
| 10.041 | COOCH₃ | benztriazol-1-yl | OCH₃ | CH₂OCH₃ | CH | 157–160° |
| 10.042 | Cl | 5(6)-nitro-benztriazol-1-yl (mixture of isomers) | OCH₃ | OCH₃ | CH | 152–155° |
| 10.043 | F | 5(6)-nitro-benztriazol-1-yl (mixture of isomers) | OCH₃ | CH₃ | CH | 147–149° |
| 10.044 | 2-Cl, 6-CH₃ | 5(6)-Nitro-benztriazol-1-yl (mixture of isomers) | OCH₃ | CH₃ | CH | 131–134° |

Formulation Examples

EXAMPLE 14

Formulation Examples for compounds of formula I (percentages are by weight)

| (a) Wettable powders | (a) | (b) | (c) |
|---|---|---|---|
| Compound of formula I | 20% | 60% | 0.5% |
| sodium lignosulfonate | 5% | 5% | 5% |
| sodium laurylsulfate | 3% | — | — |
| sodium diisobutylnaphthalenesulfonate | — | 6% | 6% |
| octylphenol polyethylene glycol ether (7–8 moles of ethylene oxide) | — | 2% | 2% |
| highly dispersed silicid acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrates | (a) | (b) |
|---|---|---|
| Compound of formula I | 10% | 1% |
| octylphenol polyethylene glycol ether | 3% | 3% |

-continued

| (b) Emulsifiable concentrates | (a) | (b) |
|---|---|---|
| (4–5 moles of ethylene oxide) | | |
| calcium dodecylbenzenesulfonate | 3% | 3% |
| castor oil polyglycol ether | 4% | 4% |
| (36 moles of ethylene oxide) | | |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| Compound of formula I | 0.1% | 1% |
| talcum | 99.9% | — |
| kaolin | — | 99% |

Dusts which are ready for use are obtained by mixing the active ingredient with the carriers, and grinding the mixture in a suitable mill.

| (d) Extruder granulate | (a) | (b) |
|---|---|---|
| Compound of formula I | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| Compound of formula | 3% |
| polyethylene glycol 200 | 2% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | (a) | (b) |
|---|---|---|
| Compound of formula I | 40% | 5% |
| ethylene glycol | 10% | 10% |
| nonylphenol polyethylene glycol ether | 6% | 1% |
| (15 moles of ethylene oxide) | | |
| sodium lignosulfonate | 10% | 5% |
| carboxymethylcellulose | 1% | 1% |
| 37% aqueous formaldehyde solution | 0.2% | 0.2% |
| silicone oil in the form of a 75% | 0.8% | 0.8% |
| aqueous emulsion | | |
| water | 32% | 77% |

The finely ground active ingredient is intimately mixed with the adjuvants, giving a suspension concentrate from which suspensions of any desired concentration can be obtained by dilution with water.

| (g) Salt solution | |
|---|---|
| Compound of formula I | 5% |
| isopropylamine | 1% |
| octylphenol polyethylene glycol ether | 3% |
| (78 moles of ethylene oxide) | |

| (g) Salt solution | |
|---|---|
| water | 91% |

Biological Examples

EXAMPLE 15

Preemergence herbicidal action

Plastic pots are filled with expanded vermiculite (density: 0.135 g/cm$^3$, water-absorbing capacity: 0.565 1/1). After the non-absorptive vermiculite has been saturated with an aqueous emulsion in deionised water which contains the test compound in a concentration of 70.8 ppm, seeds of the following plants are sown on the surface: *Nasturtium officinalis, Agrostis tenuis, Stellaria media* and *Digitaria sanguinalis*. The pots are then kept in a climatic chamber at 20° C., an illumination of about 20 lux and a relative humidity of 70%. During the germinating phase of 4 to 6 days, the pots are covered with lightpermeable material and watered with deionised water to increase the local humidity. After the 5th day, 0.5% of a commercial liquid fertiliser (Greenzit ®, ex Ciba-Geigy) is added to the water. The test is evaluated 12 days after sowing and the action on the plants is assessed according to the following rating:

| | |
|---|---|
| 1 | plants have not emerged or are totally withered |
| 2–3 | very pronounced action |
| 4–6 | medium action |
| 7–8 | weak action |
| 9 | no action (as untreated controls). |

Preemergence action:
Concentration of the test compound emulsion: 70.8 ppm

| Test plant Compound | Nasturtium | Stellaria | Agrostis | Digitaria |
|---|---|---|---|---|
| 5.001 | 2 | 2 | 2 | 2 |
| 5.004 | 1 | 1 | 1 | 1 |
| 5.007 | 1 | 1 | 1 | 1 |
| 5.022 | 2 | 2 | 2 | 2 |
| 5.051 | 2 | 2 | 2 | 2 |
| 5.061 | 2 | 2 | 2 | 2 |
| 5.064 | 1 | 1 | 1 | 1 |
| 5.066 | 1 | 1 | 1 | 1 |
| 5.089 | 2 | 1 | 1 | 2 |
| 5.102 | 2 | 1 | 1 | 2 |
| 5.105 | 1 | 1 | 1 | 1 |
| 5.107 | 1 | 1 | 1 | 1 |
| 5.121 | 2 | 2 | 2 | 2 |
| 5.124 | 2 | 2 | 2 | 2 |
| 5.130 | 2 | 2 | 2 | 2 |
| 5.133 | 2 | 2 | 2 | 2 |
| 5.142 | 2 | 2 | 2 | 2 |
| 5.165 | 1 | 2 | 1 | 2 |
| 5.170 | 2 | 2 | 2 | 2 |
| 5.229 | 2 | 2 | 2 | 2 |
| 5.230 | 2 | 2 | 2 | 2 |
| 5.231 | 2 | 2 | 2 | 2 |
| 5.232 | 2 | 1 | 1 | 2 |
| 5.235 | 2 | 2 | 2 | 2 |
| 5.236 | 2 | 1 | 1 | 2 |
| 5.237 | 2 | 2 | 2 | 2 |
| 5.238 | 2 | 1 | 2 | 2 |
| 5.239 | 2 | 1 | 1 | 1 |
| 5.240 | 2 | 2 | 2 | 2 |
| 5.241 | 2 | 2 | 2 | 2 |
| 5.242 | 2 | 2 | 2 | 2 |
| 5.243 | 2 | 3 | 2 | 3 |
| 5.244 | 2 | 3 | 2 | 3 |
| 5.246 | 3 | 4 | 3 | 5 |

-continued

| Test plant Compound | Nasturtium | Stellaria | Agrostis | Digitaria |
|---|---|---|---|---|
| 5.247 | 3 | 5 | 3 | 5 |
| 5.252 | 2 | 2 | 2 | 2 |
| 6.001 | 2 | 2 | 2 | 2 |
| 6.010 | 1 | 1 | 1 | 1 |
| 6.011 | 1 | 1 | 1 | 1 |
| 6.013 | 2 | 2 | 2 | 2 |
| 6.021 | 2 | 2 | 2 | 2 |
| 6.040 | 2 | 2 | 2 | 2 |
| 6.041 | 2 | 2 | 2 | 2 |
| 6.061 | 2 | 1 | 2 | 1 |
| 6.230 | 2 | 2 | 3 | 3 |
| 6.233 | 3 | 4 | 4 | 5 |
| 6.240 | 3 | 3 | 3 | 3 |
| 6.242 | 2 | 2 | 2 | 2 |
| 6.245 | 1 | 1 | 1 | 1 |
| 6.253 | 1 | 1 | 1 | 1 |
| 6.254 | 1 | 1 | 1 | 1 |
| 6.267 | 2 | 2 | 2 | 2 |
| 6.268 | 1 | 1 | 1 | 1 |
| 6.269 | 2 | 2 | 2 | 2 |
| 6.270 | 2 | 2 | 2 | 2 |
| 7.001 | 1 | 1 | 1 | 1 |
| 7.061 | 1 | 1 | 1 | 1 |
| 7.082 | 2 | 2 | 2 | 2 |
| 7.084 | 2 | 2 | 2 | 2 |
| 7.141 | 2 | 2 | 2 | 3 |
| 7.142 | 2 | 2 | 2 | 2 |
| 7.229 | 4 | 5 | 4 | 5 |
| 7.230 | 2 | 1 | 1 | 2 |
| 7.231 | 2 | 2 | 2 | 3 |
| 7.232 | 2 | 2 | 2 | 3 |
| 7.234 | 2 | 2 | 2 | 3 |
| 7.236 | 2 | 2 | 2 | 2 |
| 7.237 | 2 | 1 | 1 | 1 |
| 8.004 | 2 | 2 | 2 | 2 |
| 8.025 | 2 | 1 | 2 | 1 |
| 8.067 | 2 | 2 | 2 | 2 |
| 8.097 | 2 | 2 | 2 | 2 |
| 9.026 | 1 | 1 | 1 | 2 |
| 9.049 | 2 | 2 | 2 | 2 |
| 9.083 | 2 | 2 | 2 | 2 |
| 9.085 | 2 | 1 | 1 | 2 |
| 9.132 | 1 | 1 | 1 | 2 |
| 9.133 | 1 | 1 | 1 | 2 |
| 9.139 | 2 | 2 | 2 | 2 |
| 9.140 | 1 | 1 | 1 | 2 |
| 9.141 | 1 | 1 | 1 | 1 |
| 10.001 | 2 | 2 | 2 | 2 |
| 10.002 | 2 | 2 | 1 | 2 |
| 10.005 | 2 | 2 | 4 | 5 |
| 10.006 | 2 | 2 | 2 | 2 |
| 10.013 | 2 | 3 | 2 | 4 |
| 10.022 | 2 | 2 | 1 | 2 |
| 10.035 | 2 | 2 | 2 | 2 |
| 10.040 | 2 | 2 | 2 | 2 |
| 10.041 | 2 | 2 | 2 | 2 |
| 10.042 | 2 | 3 | 2 | 3 |
| 10.043 | 2 | 2 | 2 | 2 |
| 10.044 | 2 | 2 | 2 | 2 |

EXAMPLE 16

Growth inhibition of tropical cover crops

The test plants (*centrosema plumieri* and *centrosema pubescens*) are reared until fully grown and then cut back to a height of 60 cm. The plants are sprayed 7 days later with an aqueous emulsion of the test compound. The test plants are kept at 70% relative humidity and 6000 lux artificial light for 14 hours per day, at day temperatures of 27° C. and night temperatures of 21° C. and night temperatures of 21° C. The test is evaluated 4 weeks after application by assessing and weighing the new growth compared with controls and by determining the phytotoxicity.

In this test a marked reduction in new growth of the plants treated with compounds of the formula I is observed (less than 20% of the new growth of untreated control plants), without damage being caused to the test plants.

EXAMPLE 17

Growth regulation of soybeans

Soybeans of the "Hark" variety are sown in plastic containers in an earth/peat/sand mixture (6:3:1). The containers are put into a climatic chamber and the plants develop to the 5–6 trefoil leaf stage after about 5 weeks by optimum control of temperature, light, fertiliser addition, and watering. The plants are then sprayed with an aqueous mixture of a compound of the formula I until thoroughly wetted. The rate of application corresponds to 100 g a.i. per hectare. Evaluation is made about 5 weeks after application. Compared with untreated controls, the compounds of the formula I markedly increase the number and weight of the harvested siliques on the leading shoot.

EXAMPLE 18

Growth inhibition of cereals

Summar barley (*Hordeum vulgare*) and summer rye (Secale) are sown in sterilised soil in plastic beakers in a greenhouse and watered as required. The cereal shoots are treated about 21 days after sowing with an aqueous spray mixture of a compound of the formula I. The concetration corresponds to 100 g of active ingredient per hectare. Evaluation of the growth of the cereals is made 21 days after application. A comparison with untreated controls shows that the growth of cereal plants treated with compounds of the formula I is significantly reduced (60–90% of the controls) and that the diameter of the stalks has in some cases increased.

EXAMPLE 19

Growth inhibition of grasses

Seeds of the grasses *Lolium perenne*, *Poa pratensis*, *Festuca ovina*, *Dactylis glomerate* and *Cynodon dactylon* are sown in plastic dishes filled with an earth/peat/sand mixture (6:3:1), in a greenhouse, and watered as required. The emergent grasses are cut back weekly to a height of 4 cm, and about 50 days after sowing and 1 day after the last cut are sprayed with an aqueous spray mixture of a compound of the formula I. The concentration of test compound corresponds to a rate of application of up to 100 g a.i. per hectare. The growth of the grasses is evaluated 21 days after application. The compounds of formula I effect a reduction in new growth in the range of 10–30% in comparison with untreated controls.

EXAMPLE 20

Root growth

To determine the stimulation of root growth, seeds which have been dressed with 45–500 mg of active ingredient per kg of seeds as well as untreated seeds for use as controls are propagated in plastic cylinders of 5 cm diameter and 30 cm in height. 10 seeds are propagated in each cylinder. The cylinders are kept in climatic chambers under controlled conditions. Evaluation of the test is made 10 days after sowing and after carefully washing off the soil. The length and dry weight of the roots are determined and compared with the results obtained with untreated seeds.

Compared with untreated seedlings, wheat seeds treated with 100 and 200 mg of active ingredient per kg of seeds exhibited an approximately 10% increase in length and weight.

What is claimed is:

1. An N-pyrimidinyl-methylamine of the formula

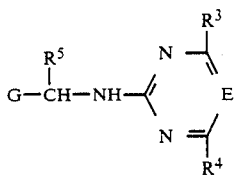

wherein
G is selected from $R^6$ and $R^9S(O)_m$
m is 0 or 2
E is —CH=,
$R^3$ is halogen, $C_1$-$C_4$alkyl, $C_1$-$C_4$alkoxy, $C_1$-$C_4$haloalkyl, $C_1$-$C_4$haloalkoxy, $C_2$-$C_4$alkoxyalkyl, $C_2$-$C_4$alkoxyalkoxy, cyclopropyl, —$NH_2$, $C_1$-$C_4$alkylamino or di($C_1$-$C_4$alkyl)amino,
$R^4$ has the same meaning as $R^3$ but independently thereof,
$R^5$ is hydrogen or $C_1$-$C_4$alkyl,
$R^6$ is a 5- to 7-membered heterocyclic radical which is bound through the nitrogen atom and which may be fused to a benzene ring, which is selected from among 1,2,4-triazole, benztriazole, benzimidazole, carbazole, indole, imidazole and pyrazole, which is unsubstituted or substituted by one or more members selected from the group consisting of nitro, halogen, and $C_1$-$C_4$alkyl,
$R^9$ is $C_1$-$C_4$alkyl which is unsubstituted or substituted by halogen, $C_2$-$C_4$alkoxy, carboxyl, $C_1$-$C_4$alkoxycarbonyl or —$CONR^{10}R^{11}$, or is a phenyl, benzyl or naphthyl radical, each of which is unsubstituted or substituted by one or more identical or different members selected from the group consisting of halogen, nitro, carboxyl, $C_1$-$C_4$alkyl, $C_1$-$C_4$haloalkyl, $C_1$-$C_4$alkoxy or $C_1$-$C_4$haloalkoxy, and $R^9$ can also be a radical selected from —CZ—$C_1$-$C_4$alkyl, —CZO—$C_1$-$C_4$alkyl, —$CZNR^{10}R^{11}$, —CZ-phenyl, CZ-benzyl or CZ-naphthyl, wherein the phenyl rings may be substituted as indicated above,
$R^{10}$ and $R^{11}$, each independently of the other, are hydrogen, $C_1$-$C_4$alkyl, $C_3$-$C_4$alkenyl, $C_3$-$C_4$alkynyl, $C_1$-$C_4$cyanoalkyl, or one of $R^{10}$ and $R^{11}$ may also be $C_1$-$C_4$alkoxy or $C_2$-$C_4$alkoxyalkyl, phenyl or benzyl, and the penyl ring may be substituted by one or more identical or different members selected from the group consisting of halogen, nitro, $C_1$-$C_4$haloalkyl or $C_1$-$C_4$alkoxy; or $R^{10}$ and $R^{11}$, together with the nitrogen atom to which they are attached, may also be a 5- to 7-membered saturated heterocycle selected from among pyrrolidine, piperidine, morpholine and azepine and which are unsubstituted or substituted by halogen or $C_1$-$C_4$alkyl and Z is oxygen or sulfur.

2. An N-pyrimidinyl-N-thiomethylamino or -sulfonylamine of the formula

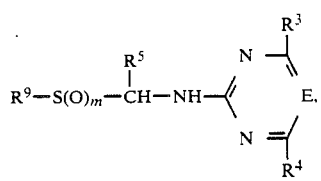

wherein E, m, $R^3$ $R^4$ and $R^9$ are as defined in claim 1.

3. An N-pyrimidinyl-heterocyclylaminomethylamine of the formula

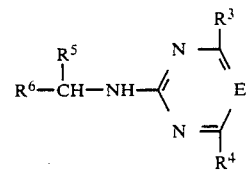

wherein $R^5$, $R^6$, E $R^3$ and $R^4$ are as defined in claim 1.

4. N-(4,6-dimethylpyrimidin-2-yl)-N-(4-chlorophenylthiomethyl)amine, according to claim 1.

5. N-(4-difluoromethoxy-6-methylpyrimidin-2-yl)-N-(4-tolylsulfonylmethyl)amine, according to claim 1.

6. N-(4-methoxy-5-methylpyrimidin-2-yl)-N-(naphthylthiomethyl)amine, according to claim 1.

7. N-(4,6-dimethylpyrimidin-2-yl)-N-pyrrolidinothiocarbonylthiomethyl)amine, according to claim 1.

8. N-(4,6-dimethylpyrimidin-2-yl)-N-(4-tolylsulfonylmethyl)amine, according to claim 1.

9. N-(4methoxy-6-methylpyrimidin-2-yl)-N-(4-tolylsulfonylmethyl)amine, according to claim 1.

10. N-(4,6-dimethylpyrimidin-2-yl)-N-(1,2,4-triazol-1-yl-methyl)amine, according to claim 1.

* * * * *